US008975227B2

(12) United States Patent
Wang et al.

(10) Patent No.: US 8,975,227 B2
(45) Date of Patent: Mar. 10, 2015

(54) INTRAORAL DOSAGE FORMS OF GLUCAGON

(75) Inventors: Nai Fang Wang, Long Island City, NY (US); Puchun Liu, Chappaqua, NY (US); Steven Dinh, Briarcliff Manor, NY (US); Michael M. Goldberg, Englewood, NJ (US); Ehud Arbit, Englewood, NJ (US)

(73) Assignee: Emisphere Technologies, Inc., Roseland, NJ (US)

( * ) Notice: Subject to any disclaimer, the term of this patent is extended or adjusted under 35 U.S.C. 154(b) by 1194 days.

(21) Appl. No.: 11/994,032

(22) PCT Filed: Jul. 17, 2006

(86) PCT No.: PCT/US2006/027901
§ 371 (c)(1),
(2), (4) Date: Dec. 27, 2007

(87) PCT Pub. No.: WO2007/011958
PCT Pub. Date: Jan. 25, 2007

(65) Prior Publication Data
US 2008/0207514 A1 Aug. 28, 2008

Related U.S. Application Data

(60) Provisional application No. 60/699,617, filed on Jul. 15, 2005.

(51) Int. Cl.
A61K 38/26 (2006.01)
C07K 14/605 (2006.01)

(52) U.S. Cl.
CPC .............. A61K 38/26 (2013.01); C07K 14/605 (2013.01)
USPC ........................... 514/11.7; 514/1.1; 530/308

(58) Field of Classification Search
CPC .............................. A61K 38/26; C07K 14/605
USPC .................................. 514/1.1, 11.7; 530/308
See application file for complete search history.

(56) References Cited

U.S. PATENT DOCUMENTS

| 5,284,657 | A | 2/1994 | Lu et al. | |
| 5,496,559 | A | 3/1996 | Fujioka et al. | |
| 5,650,386 | A | * | 7/1997 | Leone-Bay et al. | 514/2 |
| 5,866,536 | A | 2/1999 | Leone-Bay et al. | |
| 6,596,298 | B2 | 7/2003 | Leung et al. | |
| 2003/0134861 | A1 | 7/2003 | Doherty et al. | |
| 2006/0078622 | A1 | 4/2006 | Majuru et al. | |
| 2006/0078623 | A1 | 4/2006 | Dhoot et al. | |
| 2006/0160722 | A1 | * | 7/2006 | Green et al. | 514/3 |

FOREIGN PATENT DOCUMENTS

| WO | 9423767 | 10/1994 |
| WO | 9511690 | 5/1995 |
| WO | 9528838 | 11/1995 |
| WO | 9528920 | 11/1995 |
| WO | 9609813 | 4/1996 |
| WO | 9610396 | 4/1996 |
| WO | 9612473 | 5/1996 |
| WO | 9612475 | 5/1996 |
| WO | 9630036 | 10/1996 |
| WO | 9633699 | 10/1996 |
| WO | 9731938 | 9/1997 |
| WO | 9736480 | 10/1997 |
| WO | 9821951 | 5/1998 |
| WO | 9825589 | 6/1998 |
| WO | 9834632 | 8/1998 |
| WO | 9849135 | 11/1998 |
| WO | 9916427 | 4/1999 |
| WO | 0006534 | 2/2000 |
| WO | 0007979 | 2/2000 |
| WO | 0040203 | 7/2000 |
| WO | 0046182 | 8/2000 |
| WO | 0047188 | 8/2000 |
| WO | 0048589 | 8/2000 |
| WO | 0050386 | 8/2000 |
| WO | 0059480 | 10/2000 |
| WO | 0132130 | 5/2001 |
| WO | 0132596 | 5/2001 |
| WO | 0134114 | 5/2001 |
| WO | 0144199 | 6/2001 |
| WO | 0151454 | 7/2001 |
| WO | 0170219 | 9/2001 |
| WO | 0192206 | 12/2001 |
| WO | 0202509 | 1/2002 |
| WO | 0215959 | 2/2002 |
| WO | 0216309 | 2/2002 |
| WO | 0219969 | 3/2002 |
| WO | 0220466 | 3/2002 |
| WO | 02070438 | 9/2002 |
| WO | 02100338 | 12/2002 |
| WO | 03026582 | 4/2003 |
| WO | 03045306 | 6/2003 |
| WO | WO 03/072195 | * 9/2003 |

OTHER PUBLICATIONS

Glucagon from GenBank Accession No. AAB28788, pp. 1-2. Accessed Jun. 9, 2009.*
GLP-1 from GenBank Accession No. AAM09770, pp. 1-2. Accessed Jun. 9, 2009.*
Hoist JJ, "Glucagon-like peptide-1, a gastrointestinal hormone with a pharmaceutical potential," Curr. Med. Chem., 1999, 6(11): 1005-1017. Abstract only enclosed.*
Insulin and Glucagon from http://biomed.brown.edu/http://biomed.brown.edu/Courses/Bl108/Bl108_2002_Groups/pancstems/stemcell/insulin_glucagon . . . , pp. 1-2. Accessed Jun. 5, 2014.*

* cited by examiner

Primary Examiner — Julie Ha
(74) Attorney, Agent, or Firm — Blank Rome LLP

(57) ABSTRACT

The present invention provides a composition (e.g., a pharmaceutical composition) comprising at least one delivery agent compound and glucagon. Preferably, the composition includes a therapeutically effective amount of glucagon and the delivery agent compound. The composition of the present invention facilitates the delivery of glucagon and increases its bioavailability compared to administration without the delivery agent compound.

18 Claims, 8 Drawing Sheets

Buccal Tablet Administration of GLUCAGON in Dogs
GLUCAGON/SNAD: 0.1/10 mg/kg

Glucagon sublingual tablet vs. an aqueous gel formulation

Positive (Glucagon solution – IM injection) and negative (Glucagon sublingual tablet without SNAC)

Dose Optimization Study

Dose Optimization Study, n=4

Material Preparation Study

Formulation Study

Dosage Form Study

INTRAORAL DOSAGE FORMS OF GLUCAGON

This application is a national phase of International Application No. PCT/US2006/027901, filed Jul. 17, 2006, which claims the benefit of U.S. Provisional Application No. 60/699,617, filed Jul. 15, 2005. International Application No. PCT/US2006/027901 published in English on Jan. 25, 2007 under Publication No. WO 2007/011958. These applications are incorporated by reference in their entireties.

FIELD OF THE INVENTION

The present invention relates to compositions for delivering glucagon components, including glucagon. Methods for preparation, administration and treatment are also disclosed.

BACKGROUND OF THE INVENTION

Glucagon, an antihypoglycemic agent (an agent that increases serum glucose concentrations), is a hormone synthesized and secreted by the α-2 cells of the pancreatic islets of Langerhans that increases blood glucose by stimulating hepatic glyconeogenesis.

Glucagon is a linear peptide of 29 amino acids, and its administration causes a rapid rise in blood glucose making it suitable to treat severe hypoglycemia.

It is commercially available as a parenteral for injection of recombinant DNA origin (Glucagon Diagnostic Kit®, Lilly; Glucagon Emergency Kit®, Lilly; GlucaGen® Diagnostic Kit, Bedford; and most recently, GlucaGen HypoKit®, Novo Nordisk A/S). Glucagon is primarily used for the emergency treatment of severe hypoglycemia if liver glycogen is available (the hyperglycemic response is diminished in conditions associated with starvation, adrenal insufficiency, emaciated or undernourished patients, or in those with uremia or hepatic disease). It also has utility in the radiographic examination of the gastrointestinal tract (stomach, duodenum, small intestine and colon) where a hypertonic state is advantageous. For this purpose, glucagon appears to be as effective as antimuscarinics and is associated with fewer adverse effects.

Furthermore, there are numerous reports of successful utilization of glucagon as a cardiac stimulant for the management of cardiac manifestations of severe beta-blockade overdosage or calcium channel blocker overdossage. These cardiac manifestations, i.e. bradycardia, hypotension, and myocardial depression, have been successfully reverse in patients unresponsive to atropine, epinephrine, dopamine, dobutamine, inarrinone, and the like.

These and further uses may be found in AHFS Drug Information, ASHP, Bethseda, Md., 2005, which is incorporated here by reference.

Intraoral (including buccal and sublingual) administration offers significant advantages over injectable formulations. Intraoral delivery reduces hepatic and gastrointestinal first-pass metabolism and can minimize food effect. More importantly, glucagon can be delivered to a patient with severe hypoglycemia by the patient or care provider via the oral mucosa and without the need or training in the delivery of injected glucagon formulations. Accordingly, there is a need for glucagon dosage forms that can be intraorally administered.

There is also a need for formulations (including oral and intraoral formulations) that have increased bioavailability.

SUMMARY OF THE INVENTION

The present invention provides a composition (e.g., a pharmaceutical composition) comprising at least one delivery agent compound and a glucagon component (e.g. glucagon). Preferably, the composition includes a therapeutically effective amount of a glucagon component and the delivery agent compound.

In another embodiment of the present invention, the composition is an intraoral dosage form that facilitates the non-parenteral delivery of a glucagon component.

Preferred delivery agent compounds include, but are not limited to, N-(8-[2-hydroxybeinzoyl]amino)caprylic acid (SNAC) and N-(10-[2-hydroxybenzoyl]amino)decanoic acid (SNAD) and salts thereof, and solvates and hydrates thereof. In a preferred embodiment, the salt is the sodium salt, such as the monosodium salt. In one embodiment, the glucagon component is glucagons and the delivery agent is SNAC.

In one preferred embodiment, the composition comprises a glucagon component and at least one delivery agent of the following structure or a salt thereof:

Formula A wherein
Ar is phenyl or naphthyl;
Ar is optionally substituted with one or more of —OH, halogen, $C_1$-$C_4$ alkyl, $C_2$-$C_4$ alkenyl, $C_1$-$C_4$ alkoxy or $C_1$-$C_4$ haloalkoxy;
$R^7$ is selected from $C_4$-$C_{20}$ alkyl, $C_4$-$C_{20}$ alkenyl, phenyl, naphthyl, ($C_1$-$C_{10}$ alkyl) phenyl, ($C_2$-$C_{10}$ alkenyl)phenyl, ($C_1$-$C_{10}$ alkyl) naphthyl, $C_2$-$C_{10}$ alkenyl)naphthyl, phenyl ($C_1$-$C_{10}$ alkyl), phenyl ($C_2$-$C_{10}$ alkenyl), naphthyl($C_1$-$C_{10}$ alkyl), or naphthyl($C_2$-$C_{10}$ alkenyl);
$R^8$ is selected from hydrogen, $C_1$-$C_4$ alkyl, $C_2$-$C_4$ alkenyl, $C_1$-$C_4$ alkoxy, and $C_1$-$C_4$ haloalkoxy;
$R^7$ is optionally substituted with $C_1$-$C_4$ alkyl, $C_2$-$C_4$ alkenyl, $C^1$-$C_4$ alkoxy, $C_1$-$C_4$ haloalkoxy, —OH, —SH, and —$CO_2R^9$, or any combination thereof;
$R^9$ is hydrogen, $C_1$-$C_4$ alkyl, or $C_2$-$C_4$ alkenyl.
$R^7$ is optionally interrupted by oxygen, nitrogen, sulfur or any combination thereof. In some embodiments, the compounds are not substituted with an amino group in the position alpha to the acid group.

In another preferred embodiment, the composition comprises a glucagon component (e.g. glucagon), and at least one delivery agent of the following structure or a salt thereof:

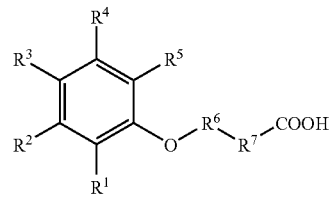

Formula B wherein
$R^1$, $R^2$, $R^3$, and $R^4$ are independently H, —OH, halogen, $C_1$-$C_4$ alkyl, $C_2$-$C_4$ alkenyl, $C_1$-$C_4$ alkoxy, —C(O)$R^8$, —$NO_2$, —$NR^9R^{10}$, or —$N^+R^9R^{10}R^{11}(R^{12})^-$;
$R^5$ is H, —OH, —$NO_2$, halogen, —$CF_3$, —$NR^4R^5$, —$N^+R^{14}R^{15}R^{16}(R^{13})^-$, amide, $C_1$-$C_{12}$ alkoxy, $C_1$-$C_{12}$ alkyl, $C_2$-$C_{12}$ alkenyl, carbamate, carbonate, urea, or —C(O)$R^{18}$;

R[5] is optionally substituted with halogen, —OH, —SH, or —COOH;

R[5] is optionally interrupted by O, N, S, or —C(O)—;

R[6] is a $C_1$-$C_{12}$ alkylene, $C_2$-$C_{12}$ alkenylene, or arylene;

R[6] is optionally substituted with a $C_1$-$C_4$ alkyl, $C_2$-$C_4$ alkenyl, $C_1$-$C_4$ alkoxy, —OH, —SH, halogen, —NH$_2$, or —CO$_2$R[8];

R[6] is optionally interrupted by O or N;

R[7] is a bond or arylene;

R[7] is optionally substituted with —OH, halogen, —C(O)CH$_3$, —NR[10]R[11], or —N$^+$R[10]R[11]R[12](R[13])$^-$;

each occurrence of R[8] is independently H, $C_1$-$C_4$ alkyl, $C_2$-$C_4$ alkenyl, or —NH$_2$;

R[9], R[10], R[11], and R[12] independently H or $C_1$-$C_{10}$ alkyl;

R[13] is a halide, hydroxide, sulfate, tetrafluoroborate, or phosphate;

R[14], R[15] and R[16] are independently H, $C_1$-$C_{10}$ alkyl, $C_1$-$C_{10}$ alkyl substituted with —COOH, $C_2$-$C_{12}$ alkenyl, $C_2$-$C_{12}$ alkenyl substituted with —COOH, or —C(O)R[17];

R[17] is —OH, $C_1$-$C_{10}$ alkyl, or $C_2$-$C_{12}$ alkenyl; and

R[18] is H, $C_1$-$C_6$ alkyl, —OH, —NR[14]R[15], or N$^+$R[14]R[15]R[16](R[13]).

Optionally, when R[1], R[2], R[3], R[4], and R[5] are H, and R[7] is a bond then R[6] is not a $C_1$-$C_6$, $C_9$ or $C_{10}$ alkyl.

Optionally, when R[1], R[2], R[3], and R[4] are H, R[5] is —OH, R[7] is a bond then R[6] is not a $C_1$-$C_3$ alkyl.

Optionally, when at least one of R[1], R[2], R[3], and R[4] is not H, R[5] is —OH, R[7] is a bond, then R[6] is not a $C_1$-$C_4$ alkyl.

Optionally, when R[1], R[2], and R[3] are H, R[4] is —OCH$_3$, R[5] is —C(O)CH$_3$, and R[6] is a bond then R[7] is not a $C_3$ alkyl.

Optionally, when R[1], R[2], R[4], and R[1] are H, R[3] is —OH, and R[7] is a bond then R[6] is not a methyl.

In yet another embodiment the composition comprises a glucagon component and at least one delivery agent of the following structure or a salt thereof:

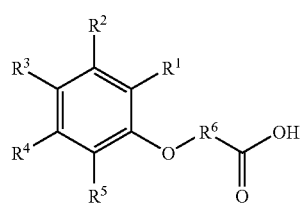

Compound C wherein

R[1], R[2], R[3], R[4] and R[5] are independently H, —CN, —OH, —OCH$_3$, or halogen, at least one of R[1], R[2], R[3], R[4] and R[5] being —CN; and R[6] is a $C_1$-$C_{12}$ linear or branched alkylene, alkenylene, arylene, alkyl(arylene) or aryl(alkylene).

According to one embodiment, when R[1] is —CN, R[4] is H or —CN, and R[2], R[3], and R[5] are H, then R[6] is not methylene ((CH$_2$)$_1$).

Also provided is a dosage unit form (e.g., an oral or intraoral dosage unit form) comprising the composition of the present invention. The dosage unit form may be in the form of a liquid or a solid, such as a tablet, capsule or particle, including a powder or sachet, and is preferable an intraoral dosage form.

Another embodiment is a method for administering glucagon to an animal in need thereof, by administering the composition or dosage unit form(s) of the present invention to the animal. The preferred route of administration is oral or intraoral.

Yet another embodiment is a method of treating hypoglycemia in an animal (such as a human) in need thereof by administering an effective amount of the composition of the present invention to the animal.

Yet another embodiment is a method for treating conditions or disorders which can be alleviated by administering to an animal (such as a human) a therapeutically effective amount of the composition or dosage unit form(s) of the present invention. Such conditions and disorders, include but are not limited to, hypoglycemia, hypoglycemia associated with excess insulin administration (e.g. insulin coma) hypoglycemia associated with excess administration of any antidiabetic medication, the radiographic examination of the gastrointestinal tract, or to treat severe cardiac manifestations (e.g. bradycardia, hypotension, myocardial depression) associated with overdosage of beta-adrenergic blockers or calcium channel blockers.

Yet another embodiment is a method of preparing a composition of the present invention by mixing at least one delivery agent compound and a glucagon component (e.g. glucagon).

Yet another embodiment is a dosage unit form for intraoral administration comprising at least one delivery agent compound and a glucagon component (e.g. glucagon). The dosage unit form may be, for example, in the form of a solid, such as a tablet or candy which dissolves in the mouth, a powder, a liquid, or a thin sheet, or any other form which dissolves and/or sticks to the interior of the mouth, or facilitates the intraoral administration of glucagon.

Yet another embodiment is a method for treating conditions or disorders which can be alleviated by reducing nutrient availability in an animal (such as a human) by intraorally administering to the animal a therapeutically effective amount of the composition or dosage unit form(s) of the present invention. Such conditions and disorders, include but are not limited to, those described above.

DETAILED DESCRIPTION OF THE INVENTION

Figure 1:
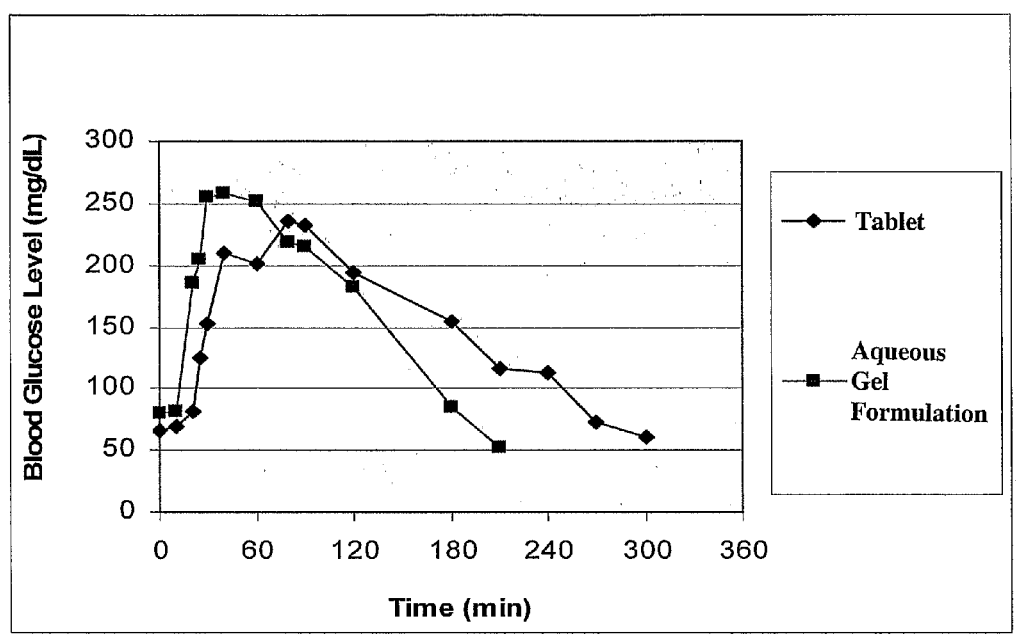
FIG. 1 is a graph of serum glucose concentrations in beagles versus time after intraoral administration of 1 mg/kg of glucagon and 100 mg/kg of SNAC compared to the same dose of oral solution of glucagon and SNAC.

Embodiments of the invention may comprise dosage unit forms for intraoral administration comprising (a) at least one glucagon, a glucagon agonist, or a mixture thereof, and (b) a delivery agent of the formula:

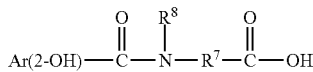

Formula A and salts thereof, wherein:

Ar is phenyl or naphthyl;

Ar is optionally substituted with one or more of —OH, halogen, $C_1$-$C_4$ alkyl, $C_2$-$C_4$ alkenyl, $C_1$-$C_4$ alkoxy or $C_1$-$C_4$ haloalkoxy;

$R^7$ is selected from $C_4$-$C_{20}$ alkyl, $C_4$-$C_{20}$ alkenyl, phenyl, naphthyl, ($C_1$-$C_{10}$ alkyl) phenyl, $C_2$-$C_{10}$ alkenyl)phenyl, ($C_1$-$C_{10}$ alkyl) naphthyl, ($C_2$-$_{10}$alkenyl)naphthyl, phenyl ($C_1$-$C_{10}$ alkyl), phenyl ($C_2$-$C_{10}$ alkenyl), naphthyl($C_1$-$C_{10}$ alkyl), or naphthyl($C_2$-$C_{10}$ alkenyl);

$R^8$ is selected from hydrogen, $C_1$-$C_4$ alkyl, to $C_2$-$C_4$ alkenyl, $C_1$-$C_4$ alkoxy, and $C_1$-$C_4$ haloalkoxy;

$R^7$ is optionally substituted with $C_1$-$C_4$ alkyl, $C_2$-$C_4$ alkenyl, $C_1$-$C_4$ alkoxy, $C_1$-$C_4$ haloalkoxy, —OH, —SH, and —$CO_2R^9$, or any combination thereof;

$R^9$ is hydrogen, $C_1$-$C_4$ alkyl, or $C_2$-$C_4$ alkenyl; and $R^7$ is optionally interrupted by oxygen, nitrogen, sulfur or any combination thereof. In some embodiments, the compounds are not substituted with an amino group in the position alpha to the acid group.

Embodiments of the invention may comprise dosage unit forms for intraoral administration comprising (a) at least one glucagon component and (b) a delivery agent of the formula

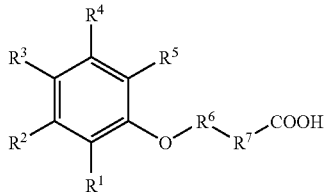

Formula B and salts thereof, wherein $R^1$, $R^2$, $R^3$, and $R^4$ are independently H, —OH, halogen, $C_1$-$C_4$ alkyl, $C_2$-$C_4$ alkenyl, $C_1$-$C_4$ alkoxy, —C(O)$R^8$, —$NO_2$, —$N^+R^9R^{10}$, or —$N^+R^9R^{10}R^{11}(R^{12})^-$;

$R^5$ is H, —OH, —$NO_2$, halogen, —$CF_3$, —$NR^{14}R^{15}$, —$N^+R^{14}R^{15}R^{16}(R^{13})^-$, amide, $C_1$-$C_{12}$ alkoxy, $C_1$-$C_{12}$ alkyl, $C_2$-$C_{12}$ alkenyl, carbamate, carbonate, urea, or —C(O)$^{18}$;

$R^5$ is optionally substituted with halogen, —OH, —SH, or —COOH;

$R^5$ is optionally interrupted by O, N, S, or —C(O)—;

$R^6$ is a $C_1$-$C_{12}$ alkylene, $C_2$-$C_{12}$ alkenylene, or arylene;

$R^6$ is optionally substituted with a $C_1$-$C_4$ alkyl, $C_2$-$C_4$ alkenyl, $C_1$-$C_4$ alkoxy, —OH, —SH, halogen, —$NH_2$, or —$CO_2R^8$;

$R^6$ is optionally interrupted by O or N;

$R^7$ is a bond or arylene;

$R^7$ is optionally substituted with —OH, halogen, —C(O)$CH_3$, —$NR^{10}R^{11}$, or —$N^+R^{10}R^{11}R^{12}(R^{13})^-$;

$R^8$ is H, $C_1$-$C_4$ alkyl, $C_2$-$C_4$ alkenyl, or —$NH_2$;

$R^9$, $R^{10}$, $R^{11}$, and $R^{12}$ independently H or $C_1$-$C_{10}$ alkyl;

$R^{13}$ is a halide, hydroxide, sulfate, tetrafluoroborate, or phosphate; and $R^{14}$, $R^{15}$ and $R^{16}$ are independently H, $C_1$-$C_{10}$ alkyl, $C_1$-$C_{10}$ alkyl substituted with —COOH, $C_2$-$C_{12}$ alkenyl, $C_2$-$C_{12}$ alkenyl substituted with —COOH, —C(O)$R^{17}$;

$R^{17}$ is —OH, $C_1$-$C_{10}$ alkyl, or $C_2$-$C_{12}$ alkenyl; and $R^{18}$ is H, $C_1$-$C_6$ alkyl, —OH, —$NR^{14}R^{15}$, or $N^+R^{14}R^{15}R^{16}(R^{13})$.

Embodiments of the invention may comprise dosage unit forms for intraoral administration comprising a glucagon component (e.g. glucagon or a glucagon agonist) and a delivery agent of the formula

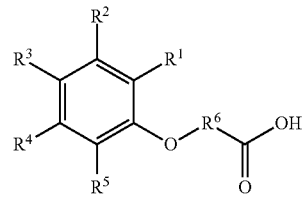

Formula C and salts thereof, wherein $R^1$, $R^2$, $R^3$, $R^4$ and $R^5$ are independently H, —CN, —OH, —$OCH_3$, or halogen, at least one of $R^1$, $R^2$, $R^3$, $R^4$ and $R^5$ being —CN; and $R^6$ is $C_1$-$C_{12}$ linear or branched alkylene, alkenylene, arylene, alkyl(arylene) or aryl(alkylene).

Embodiments of the invention may comprise a delivery agent selected from the group comprising the monosodium salt of N-(8-[2-hydroxybenzoyl]-amino)caprylic acid, the monosodium salt of N-(10-[2-hydroxybenzoyl]-amino)decanoic acid, the monosodium salt of 8-(2-hydroxy-4-methoxybenzoylamino)octanoic acid, the monosodium salt of 8-(2,6-dihydroxybenzoylamino)octanoic acid, the monosodium salt of 8-(2-hydroxy-5-bromobenzoylamino)octanoic acid, the monosodium salt 8-(2-hydroxy-5-chlorobenzoylamino)octanoic acid, the monosodium salt of 8-(2-hydroxy-5-iodobenzoylamino)octanoic acid, the monosodium salt of 8-(2-hydroxy-5-methylbenzoylamino)octanoic acid, the monosodium salt of 8-(2-hydroxy-5-fluorobenzoylamino) octanoic acid, the monosodium salt of 8-(2-hydroxy-5-methoxybenzoylamino)octanoic acid, the monosodium salt of 8-(3-hydroxyphenoxy)octanoic acid, the monosodium salt of 8-(4-hydroxyphenoxy)octanoic acid, the monosodium salt of 6-(2-cyanophenoxy)hexanoic acid, the monosodium salt of 8-(2-Hydroxyphenoxy)octyl-diethanolamine, disodium salt of N-(10-[2-hydroxybenzoyl]-amino)decanoic acid, the disodium salt of 8-(4-hydroxyphenoxy)octanoate, the monosodium salt of 8-(4-hydroxyphenoxy)octanoate, the disodium salt of 8-(2-hydroxy-4-methoxybenzoylamino)octanoic acid, and the disodium salt of 8-(2-hydroxy-5-methoxybenzoylamino)octanoic acid.

Embodiments of the invention may comprise a delivery agent N-(8-[2-hydroxybenzoyl]-amino)caprylic acid or a pharmaceutically acceptable salt thereof, or N-(10-[2-hydroxybenzoyl]-amino)decanoic acid or a pharmaceutically acceptable salt thereof.

Embodiments of the invention may comprise any dosage unit form described above with an excipient, a diluent, a disintegrant, a lubricant, a plasticizer, a colorant, a dosing vehicle, or any combination thereof.

Embodiments of the invention may comprise dosage unit forms in the form of, e.g., a tablet, a capsule, a particle, a powder, a sachet, or a liquid.

Embodiments of the invention may comprise a dosing vehicle which is a liquid selected from the group comprising, e.g., water, aqueous propylene glycol, phosphate buffer, 1,2-propane diol, ethanol, Klucel® or any combination thereof.

Embodiments of the invention may comprise methods for administering an effective amount of glucagon, a glucagon agonist or a combination thereof, to a patient in need thereof, comprising the step of intraorally administering any of the dosage unit forms described above. The glucagon may be combined with the delivery agent, e.g., N-(8-[2-hydroxybenzoyl]amino)caprylic acid or N-(10-[2-hydroxybenzoyl]-amino)decanoic acid or a pharmaceutically acceptable salt thereof.

Embodiments of the invention may comprise methods of treating hypoglycemia in a patient in need thereof, comprising the step of administering to the patient an effective amount of any of the dosage unit forms described above.

Embodiments of the invention may comprise methods of treating a condition or disorder that may be alleviated by reducing nutrient availability in a patient in need thereof, comprising the step of administering to an animal an effective amount of any of the dosage unit forms described above. The condition or disorder may, e.g., be selected from the group comprising hypoglycemia, bradycardia, hypotension, and myocardial depression or any combination thereof.

Embodiments of the invention may comprise methods of improving the bioavailability of glucagon or in an animal, the method comprising the step of administering any of the dosage unit forms described above.

Embodiments of the invention may comprise methods of preparing a dosage unit form comprising the step of mixing of glucagon and a delivery agent of the formula:

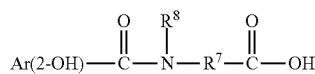

Formula A or a salt thereof, wherein:

Ar is phenyl or naphthyl;

Ar is optionally substituted with one or more of —OH, halogen, $C_1$-$C_4$ alkyl, $C_2$-$C_4$ alkenyl, $C_1$-$C_4$ alkoxy or $C_1$-$C_4$ haloalkoxy;

$R^7$ is selected from $C_4$-$C_{20}$ alkyl, $C_4$-$C_{20}$ alkenyl, phenyl, naphthyl, ($C_1$-$C_{10}$ alkyl) phenyl, $C_2$-$C_{10}$ alkenyl)phenyl, ($C_1$-$C_{10}$ alkyl) naphthyl, $C_2$-$C_{10}$ alkenyl)naphthyl, phenyl($C_1$-$C_{10}$ alkyl), phenyl($C_2$-$C_{10}$ alkenyl), naphthyl($C_1$-$C_{10}$ alkyl), or naphthyl($C_2$-$C_{10}$ alkenyl);

$R^8$ is selected from hydrogen, $C_1$-$C_4$ alkyl, $C_2$-$C_4$ alkenyl, $C_1$-$C_4$ alkoxy, and $C_1$-$C_4$ haloalkoxy;

$R^7$ is optionally substituted with $C_1$-$C_4$ alkyl, $C_2$-$C_4$ alkenyl, $C_1$-$C_4$ alkoxy, $C_1$-$C_4$ haloalkoxy, —OH, —SH, and —$CO_2R^9$, or any combination thereof;

$R^9$ is hydrogen, $C_1$-$C_4$ alkyl, or $C_2$-$C_4$ alkenyl; and $R^7$ is optionally interrupted by oxygen, nitrogen, sulfur or any combination thereof.

Definitions

The term "glucagon component" refers to all forms of glucagon, including, but not limited to naturally occurring glucagon, glucagon produced by recombinant DNA technology, or glucagon produced by or derived from any other means. Glucagon components also include fragments, agonists, and analogs of glucagon which have the same or similar pharmacological activity as glucagon.

The term "hydrate" as used herein includes, but is not limited to, (i) a substance containing water combined in the molecular form and (ii) a crystalline substance containing one or more molecules of water of crystallization or a crystalline material containing free water.

The term "solvate" as used herein includes, but is not limited to, a molecular or ionic complex of molecules or ions of a solvent with molecules or ions of the delivery agent compound or salt thereof, or hydrate or solvate thereof.

The term "delivery agent" refers to any of the delivery agent compounds disclosed herein.

The term "SNAC" refers to the monosodium salt of N-(8-[2-hydroxybenzoyl]-amino)caprylic acid.

The term "SNAD" refers to the monosodium salt of N-(10-[2-hydroxybenzoyl]-amino)decanoic acid. The term "disodium salt of SNAD" refers to the disodium salt of N-(10-[2-hydroxybenzoyl]-amino)decanoic acid.

An "effective amount of glucagon" is an amount of glucagon which is effective to treat or prevent a condition in a living organism to whom it is administered over some period of time, e.g., provides a therapeutic effect during a desired dosing interval.

An "effective amount of delivery agent" is an amount of the delivery agent which enables and/or facilitates the absorption of a desired amount of glucagon via any route of administration (such as those discussed in this application including, but not limited to, the oral (e.g., across a biological membrane in the gastrointestinal tract), nasal, pulmonary, dermal, intraoral, vaginal, and/or ocular route).

The term "AUC" as used herein, means area under the plasma concentration-time curve, as calculated by the trapezoidal rule over the complete dosing interval, e.g., 24-hour interval.

The term "mean", when preceding a pharmacokinetic value (e.g., mean Peak) represents the arithmetic mean value of the pharmacokinetic value unless otherwise specified.

As used herein and in the appended claims, the singular forms "a," "an," and "the," include plural referents unless the context clearly indicates otherwise. Thus, for example, reference to "a molecule" includes one or more of such molecules, "a reagent" includes one or more of such different reagents, reference to "an antibody" includes one or more of such different antibodies, and reference to "the method" includes reference to equivalent steps and methods known to those of ordinary skill in the art that could be modified or substituted for the methods described herein.

The term "about" generally means within 10%, preferably within 5%, and more preferably within 1% of a given value or range.

The terms "alkyl" and "alkenyl" as used herein include linear and branched alkyl and alkenyl substituents, respectively.

The term "patient" as used herein refers to a mammal and preferably a human.

The phrase "pharmaceutically acceptable" refers to additives or compositions that are physiologically tolerable when administered to a mammal.

The terms "intraoral administration" and "intraorally administering" include administration by adsorption through any surface inside the mouth or upper throat (such as the cheek (e.g., the inner cheek lining), gums, palate, tongue, tonsils, periodontal tissue, lips, and the mucosa of the mouth and pharynx). These terms, for example, include sublingual and buccal administration.

Delivery Agent Compounds

The delivery agent compound may be any of those described in U.S. Pat. Nos. 5,650,386 and 5,866,536 and International Publication Nos. WO94/23767, WO95/11690, WO95/28920, WO95/28838, WO96/10396, WO96/09813, WO96/12473, WO96/12475, WO96/30036, WO96/33699, WO97/31938, WO97/36480, WO98/21951, WO98/25589, WO98/34632, WO98/49135, WO99/16427, WO00/06534, WO00/07979, WO00/40203, WO00/46182, WO00/47188, WO00/48589, WO00/50386, WO00/59863, WO00/59480, WO01/32130, WO01/32596, WO01/34114, WO01/44199, WO01/51454, WO01/70219, WO01/92206, WO02/02509, WO02/15959, WO02/16309, WO02/20466, WO02/19969, WO02/070438, WO03/026582, WO02/100338, WO03/045306, and WO0326582, all of which are hereby incorporated by reference.

Non-limiting examples of delivery agent compounds include N-(8-[2-hydroxybenzoyl]-amino)caprylic acid, N-(10-[2-hydroxybenzoyl]-amino)decanoic acid, 8-(2-hydroxy-4-methoxybenzoylamino)octanoic acid, 8-(2,6-dihydroxybenzoylamino)octanoic acid, 8-(2-hydroxy-5-bromobenzoylamino)octanoic acid, 8-(2-hydroxy-5-chlorobenzoylamino)octanoic acid, 8-(2-hydroxy-5-iodobenzoylamino)octanoic acid, 8-(2-hydroxy-5-methylbenzoylamino)octanoic acid, 8-(2-hydroxy-5-fluorobenzoylamino)octanoic acid, 8-(2-hydroxy-5-methoxybenzoylamino)octanoic acid, 8-(3-hydroxyphenoxy)octanoic acid, 8-(4-hydroxyphenoxy) octanoic acid, 6-(2-cyanophenoxy)hexanoic acid, 8-(2-Hydroxyphenoxy)octyl-diethanolamine, 8-(4-hydroxyphenoxy)octanoate, 8-(4-hydroxyphenoxy) octanoate, 8-(2-hydroxy-4-methoxybenzoylamino)octanoic acid, 8-(2-hydroxy-5-methoxybenzoylamino)octanoic acid, and salts thereof. Preferred salts include, but are not limited to, monosodium and disodium salts.

The delivery agent compounds may be in the form of the carboxylic acid or pharmaceutically acceptable salts thereof, such as sodium salts, and hydrates and solvates thereof. The salts may be mono- or multi-valent salts, such as monosodium salts and disodium salts. The delivery agent compounds may contain different counter ions chosen for example due to their effect on modifying the dissolution profile of the carrier.

The delivery agent compounds may be prepared by methods known in the art, such as those discussed in the aforementioned publications (e.g., International Publication Nos. WO 98/34632, WO 00/07979, WO 01/44199, WO 01/32596, WO 02/20466, and WO 03/045306). SNAC, SNAD, and the free acid and other salts thereof may be prepared by any method known in the art, such as those described in U.S. Pat. Nos. 5,650,386 and 5,866,536.

The delivery agent compound may be selected from the following compounds, and pharmaceutically acceptable salts thereof:

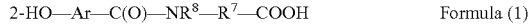

2-HO—Ar—C(O)—NR$^8$—R$^7$—COOH  Formula (1)

wherein

Ar is phenyl or naphthyl, optionally substituted with OH, halogen, $C_1$-$C_4$ alkyl, $C_1$-$C_4$ alkenyl, $C_1$-$C_4$ alkoxy or $C_1$-$C_4$ haloalkoxy;

R$^7$ is $C_4$-$C_{20}$ alkyl, $C_4$-$C_{20}$ alkenyl, phenyl, naphthyl, ($C_1$-$C_{10}$ alkyl)phenyl, ($C_1$-$C_{10}$ alkenyl)phenyl, ($C_1$-$C_{10}$ alkyl) naphthyl, ($C_1$-$C_{10}$ alkenyl) naphthyl, phenyl($C_1$-$C_{10}$ alkyl), phenyl($C_1$-$C_{10}$ alkenyl), naphthyl($C_1$-$C_{10}$ alkyl), or naphthyl ($C_1$-$C_{10}$ alkenyl);

R$^8$ is hydrogen, $C_1$ to $C_4$ alkyl, $C_2$ to $C_4$ alkenyl, $C_1$ to $C_4$ alkoxy, $C_1$-$C_4$ or haloalkoxy;

R$^7$ is optionally substituted with $C_1$ to $C_4$ alkyl, $C_2$ to $C_4$ alkenyl, $C_1$ to $C_4$ alkoxy, $C_1$-$C_4$ haloalkoxy, —OH, —SH, and —CO$_2$R$^9$ or any combination thereof;

R$^9$ is hydrogen, $C_1$ to $C_4$ alkyl or $C_2$ to $C_4$ alkenyl; and

R$^7$ is optionally interrupted by oxygen, nitrogen, sulfur or any combination thereof; with the proviso that the compounds are not substituted with an amino group in the position alpha to the acid group;

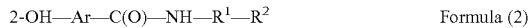

2-OH—Ar—C(O)—NH—R$^1$—R$^2$  Formula (2)

wherein

Ar is phenyl or naphthyl;

Ar is optionally substituted with $C_1$-$C_4$ alkyl, $C_1$-$C_4$ alkoxy, $C_2$-$C_4$ alkenyl, $C_2$-$C_4$ alkynyl, aryl, aryloxy, a heterocyclic ring, $C_5$-$C_7$ carbocyclic ring, halogen, —OH, —SH, CO$_2$R$^6$, —NR$^7$R$^8$, or —N$^+$R$^7$R$^8$R$^9$Y$^-$;

(a) R$^1$ is $C_1$-$C_{16}$ alkylene, $C_2$-$C_{16}$ alkenylene, $C_2$-$C_{16}$ alkynylene, $C_6$-$C_{16}$ arylene, ($C_1$-$C_{16}$ allyl)arylene, or aryl ($C_1$-$C_{16}$ alkylene);

R$^2$ is —NR$^3$R$^4$ or —N$^+$R$^3$R$^4$R$^5$Y$^-$;

R$^3$ and R$^4$ are independently hydrogen; oxygen; hydroxy; substituted or unsubstituted $C_1$-$C_{16}$ alkyl; substituted or unsubstituted $C_2$-$C_{16}$ alkenyl; substituted or unsubstituted $C_2$-$C_{16}$ alkynyl; substituted or unsubstituted aryl; substituted or unsubstituted alkylcarbonyl; substituted or unsubstituted arylcarbonyl; substituted or unsubstituted alkanesulfinyl; substituted or unsubstituted arylsulfinyl; substituted or unsubstituted alkanesulfonyl; substituted or unsubstituted arylsulfonyl; substituted or unsubstituted alkoxycarbonyl; substituted or unsubstituted aryloxycarbonyl;

R$^5$ is independently hydrogen; substituted or unsubstituted $C_1$-$C_{16}$ alkyl; substituted or unsubstituted $C_2$-$C_{16}$ alkenyl; substituted or unsubstituted $C_2$-$C_{16}$ alkynyl; substituted or unsubstituted aryl; substituted or unsubstituted alkylcarbonyl; substituted or unsubstituted arylcarbonyl; substituted or unsubstituted alkanesulfinyl; substituted or unsubstituted arylsulfinyl; substituted or unsubstituted alkanesulfonyl; substituted or unsubstituted arylsulfonyl; substituted or unsubstituted alkoxycarbonyl; substituted or unsubstituted aryloxycarbonyl;

(b) R$^1$, R$^2$, and R$^5$ are as defined above; and

R$^3$ and R$^4$ are combined to form a 5, 6 or 7-membered heterocyclic ring; or 5, 6 or 7-membered heterocyclic ring substituted with a $C_1$-$C_6$ alkyl, $C_1$-$C_6$ alkoxy, aryl, aryloxy, oxo group or carbocyclic ring; or (c) R$^2$ and R$^5$ are as defined above; and R$^1$ and R$^3$ are combined to form a 5, 6 or 7-membered heterocyclic ring; or 5, 6 or 7-membered heterocyclic ring substituted with a $C_1$-$C_6$ allyl, alkoxy, aryl, aryloxy, or oxo group or carbocyclic ring;

R$^4$ is hydrogen; oxygen; hydroxy; substituted or unsubstituted $C_1$-$C_{16}$ alkyl; substituted or unsubstituted $C_2$-$C_{16}$ alkenyl; substituted or unsubstituted $C_2$-$C_{16}$ alkynyl; substituted or unsubstituted aryl; substituted or unsubstituted alkylcarbonyl; substituted or unsubstituted arylcarbonyl; substituted or unsubstituted alkanesulfinyl; substituted or unsubstituted arylsulfinyl; substituted or unsubstituted alkanesulfonyl; substituted or unsubstituted arylsulfonyl; substituted or unsubstituted alkoxycarbonyl; substituted or unsubstituted aryloxycarbonyl;

R$^6$ is hydrogen; $C_1$-$C_4$ alkyl; $C_1$-$C_4$ alkyl substituted halogen or —OH; $C_2$-$C_4$ alkenyl; or $C_2$-$C_4$ alkenyl substituted halogen or —OH;

R$^7$, R$^8$, and R$^9$ are independently hydrogen; oxygen; $C_1$-$C_4$ alkyl; $C_1$-$C_4$ alkyl substituted with halogen or —OH; $C_2$-$C_4$ alkenyl; or $C_2$-$C_4$ alkenyl substituted with halogen or —OH; and Y is halogen, hydroxide, sulfate, nitrate, phosphate, alkoxy, perchlorate, tetrafluoroborate, or carboxylate;

Formula (3)

$$\text{Structure: benzene ring with } R^4, R^3, R^2, R^1 \text{ substituents, OH, and C(O)NH-R^5-C(O)OH group}$$

wherein $R^1$, $R^2$, $R^3$, and $R^4$ are independently hydrogen, —OH, —NR$^6$R$^7$, halogen, $C_1$-$C_4$ alkyl, or $C_1$-$C_4$ alkoxy;

$R^5$ is a substituted or unsubstituted $C_2$-$C_{16}$ alkylene, substituted or unsubstituted $C_2$-$C_{16}$ alklenylene, substituted or unsubstituted $C_1$-$C_{12}$ alkyl(arylene), or substituted or unsubstituted aryl($C_1$-$C_{12}$ alkylene); and $R^6$ and $R^7$ are independently hydrogen, oxygen, or $C_1$-$C_4$ alkyl;

Formula (4)

$$\text{Structure: benzene ring with } R^4, R^3, R^2, R^1, R^5 \text{ substituents and O-R^6-R^7 group}$$

wherein (a) $R^1$, $R^2$, $R^3$, and $R^4$ are independently H, —OH, halogen, $C_1$-$C_4$ alkyl, $C_1$-$C_4$ alkenyl, $C_1$-$C_4$ alkoxy, —C(O)R$^8$, —NO$_2$, —NR$^9$R$^{10}$, or —N$^+$R$^9$R$^{10}$R$^{11}$(Y$^-$);
  $R^8$ is hydrogen, —OH, $C_1$-$C_6$ alkyl, $C_1$-$C_4$ alkyl substituted with halogen or —OH, $C_2$-$C_4$ alkenyl unsubstituted or substituted with halogen or —OH, or —NR$^{14}$R$^{15}$;
  $R^9$, $R^{10}$, and $R^{11}$ are independently hydrogen, oxygen, $C_1$-$C_4$ alkyl unsubstituted or substituted with halogen or —OH, $C_2$-$C_4$ alkenyl unsubstituted or substituted with halogen or —OH;
  Y is halide, hydroxide, sulfate, nitrate, phosphate, alkoxy, perchlorate, tetrafluoroborate, carboxylate, mesylate, fumerate, malonate, succinate, tartrate, acetate, gluconate, maleate;
  $R^5$ is H, —OH, —NO$_2$, halogen, CF$_3$, —NR$^4$R$^5$, —N$^+$R$^{14}$R$^{15}$R$^{16}$(Y$^-$), amide, $C_1$-$C_{12}$ alkoxy, $C_1$-$C_{12}$ alkyl, $C_2$-$C_{12}$ alkenyl, carbamate, carbonate, urea, or —C(O)R$^{22}$; $R^5$ is optionally substituted with halogen, —OH, —SH, or —COOH; $R^5$ is optionally interrupted by O, N, S, or —C(O)—;
  $R^4$, $R^{15}$, and $R^{16}$ are independently H or $C_1$-$C_{10}$ alkyl;
  $R^{22}$ is H, $C_1$-$C_6$ alkyl, —OH, —NR$^{14}$R$^{15}$;
  $R^6$ is substituted or unsubstituted $C_1$-$C_{16}$ alkylene, $C_2$-$C_{16}$ alkenylene, $C_2$-$C_{16}$ alkynylene, $C_5$-$C_{16}$ arylene, ($C_1$-$C_{16}$ alkyl) arylene or aryl($C_1$-$C_{16}$ alkylene); $R^6$ is optionally substituted with $C_1$-$C_7$ alkyl or $C_1$-$C_7$ cycloalkyl;
  $R^7$ is —NR$^{15}$R$^{19}$ or —N$^+$R$^{18}$R$^{19}$R$^{20}$Y$^-$;
  $R^{18}$ and $R^{19}$ are independently hydrogen, oxygen, hydroxy, substituted or unsubstituted $C_1$-$C_{16}$ alkyl, substituted or unsubstituted $C_2$-$C_{16}$ alkenyl, substituted or unsubstituted $C_2$-$C_{16}$ alkynyl, substituted or unsubstituted aryl, substituted or unsubstituted alkylcarbonyl (e.g. substituted or unsubstituted ($C_{1-6}$ alkyl)carbonyl), substituted or unsubstituted arylcarbonyl, substituted or unsubstituted alkanesulfinyl (e.g. substituted or unsubstituted ($C_{1-6}$ alkane)sulfinyl), substituted or unsubstituted arylsulfinyl, substituted or unsubstituted alkanesulfonyl (e.g. substituted or unsubstituted ($C_{1-6}$ alkane)sulfonyl), substituted or unsubstituted arylsulfonyl, substituted or unsubstituted alkoxycarbonyl (e.g. substituted or unsubstituted ($C_{1-6}$ alkoxy)carbonyl), or substituted or unsubstituted aryloxycarbonyl, or substituted or unsubstituted $C_5$-$C_7$ heterocyclic ring (i.e., 5, 6, or 7-membered heterocyclic ring), wherein the substitutions may be halogen or —OH; and $R^{20}$ is independently hydrogen, substituted or unsubstituted $C_1$-$C_{16}$ alkyl, substituted or unsubstituted $C_2$-$C_{16}$ alkenyl, substituted or unsubstituted $C_2$-$C_{16}$ alkynyl, substituted or unsubstituted aryl, substituted or unsubstituted alkylcarbonyl (e.g. substituted or unsubstituted ($C_{1-6}$ alkyl)carbonyl), substituted or unsubstituted arylcarbonyl, substituted or unsubstituted alkanesulfinyl (e.g. substituted or unsubstituted ($C_{1-6}$ alkane)sulfinyl), substituted or unsubstituted arylsulfinyl, substituted or unsubstituted alkanesulfonyl (e.g. substituted or unsubstituted ($C_{1-6}$ alkane)sulfonyl), substituted or unsubstituted arylsulfonyl, substituted or unsubstituted alkoxycarbonyl (e.g. substituted or unsubstituted ($C_{1-6}$ alkoxy) carbonyl), or substituted or unsubstituted aryloxycarbonyl; or (b) $R^1$-$R^{16}$ and $R^{20}$ are as defined above; and
$R^{18}$ and $R^{19}$ combine to form a 5, 6, or 7-membered heterocyclic ring optionally interrupted with an oxo group and unsubstituted or substituted with $C_1$-$C_6$ alkyl, $C_1$-$C_6$ alkoxy, aryl, aryloxy, or carbocyclic ring;

Formula (5)

$$\text{Structure: benzene ring with } R^4, R^3, R^2, R^1, R^5 \text{ substituents and O-R^6-R^7-COOH group}$$

wherein $R^1$, $R^2$, $R^3$, and $R^4$ are independently H, —OH, halogen, $C_1$-$C_4$ alkyl, $C_2$-$C_4$ alkenyl, $C_1$-$C_4$ alkoxy, —C(O)R$^8$, —NO$_2$, —NR$^9$R$^{10}$, or —N$^+$R$^9$R$^{10}$R$^{11}$(R$^2$)$^-$;

$R^5$ is H, —OH, —NO$_2$, halogen, —CF$_3$, —NR$^{14}$R$^{15}$, —N$^+$R$^{14}$R$^{15}$R$^{16}$(R$^{13}$)$^-$, amide, $C_1$-$C_{12}$ alkoxy, $C_1$-$C_{12}$ alkyl, $C_2$-$C_{12}$ alkenyl, carbamate, carbonate, urea, or —C(O)R$^{18}$;

$R^5$ is optionally substituted with halogen, —OH, —SH, or —COOH;

$R^5$ is optionally interrupted by O, N, S, or —C(O)—;

$R^6$ is a $C_1$-$C_{12}$ alkylene, $C_2$-$C_{12}$ alkenylene, or arylene;

$R^6$ is optionally substituted with a $C_1$-$C_4$ alkyl, $C_2$-$C_4$ alkenyl, $C_1$-$C_4$ alkoxy, —OH, —SH, halogen, —NH$_2$, or —CO$_2$R$^8$;

$R^6$ is optionally interrupted by O or N;

$R^7$ is a bond or arylene;

$R^7$ is optionally substituted with —OH, halogen, —C(O) CH$_3$, —NR$^{10}$R$^{11}$, or —N$^+$R$^{10}$R$^{11}$R$^{12}$(R$^{13}$)$^-$;

$R^8$ is H, $C_1$-$C_4$ alkyl, $C_2$-$C_4$ alkenyl, or —NH$_2$;

$R^9$, $R^{10}$, $R^{11}$, and $R^{12}$ independently H or $C_1$-$C_{10}$ alkyl;

$R^{13}$ is a halide, hydroxide, sulfate, tetrafluoroborate, or phosphate; and $R^{14}$, $R^{15}$ and $R^{16}$ are independently H, $C_1$-$C_{10}$ alkyl, $C_1$-$C_{10}$ alkyl substituted with —COOH, $C_2$-$C_{12}$ alkenyl, $C_2$-$C_{12}$ alkenyl substituted with —COOH, —C(O)$R^{17}$;

$R^{17}$ is —OH, $C_1$-$C_{10}$ alkyl, or $C_2$-$C_{12}$ alkenyl; and $R^{18}$ is H, $C_1$-$C_6$ alkyl, —OH, —NR$^{14}$R$^{15}$, or N$^{14}$R$^{15}$R$^{16}$($R^{13}$); and

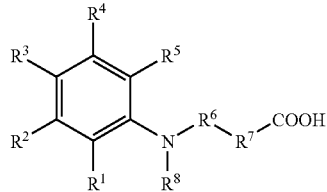

Formula (6)

wherein $R^1$, $R^2$, $R^3$, and $R^4$ are independently H, —OH, halogen, —OCH$_3$, —NR$^{10}$R$^{11}$ or —N$^+$R$^{10}$R$^{11}$R$^{12}$($R^{13}$)$^-$;

$R^5$ is H, —OH, —NO$_2$, —NR$^{14}$R$^{15}$, —N$^+$R$^{14}$R$^{15}$R$^{16}$($R^{13}$)$^-$, amide, $C_1$-$C_{12}$ alkoxy, $C_1$-$C_{12}$ alkyl, $C_2$-$C_{12}$ alkenyl, carbamate, carbonate, urea, or —C(O)$R^{18}$;

$R^5$ is optionally substituted with —OH, —SH, or —COOH;

$R^5$ is optionally interrupted by O, N, S, or —C(O)$^-$;

$R^6$ is a $C_1$-$C_{12}$ alkylene, $C_1$-$C_{12}$ alkenylene, or arylene;

$R^6$ is optionally substituted with a $C_1$-$C_4$ alkyl, $C_2$-$C_4$ alkenyl, $C_1$-$C_4$ alkoxy, —OH, —SH, halogen, —NH$_2$, or —CO$_2$R$^9$;

$R^6$ is optionally interrupted by O or N;

$R^7$ is a bond or arylene;

$R^7$ is optionally substituted with —OH, halogen, —C(O)CH$_3$, —NR$^{10}$R$^{11}$ or —N$^+$R$^{10}$R$^{11}$R$^{12}$($R^{13}$)$^-$;

$R^8$ is H or $C_1$-$C_4$ alkyl;

$R^9$ is H, $C_1$-$C_4$ alkyl, or $C_2$-$C_4$ alkenyl;

$R^{10}$, $R^{11}$, and $R^{12}$ are independently H or $C_1$-$C_{10}$ alkyl;

$R^{13}$ is a halide, hydroxide, sulfate, tetrafluoroborate, or phosphate;

$R^{14}$, $R^{15}$, and $R^{16}$ are independently H, $C_1$-$C_{10}$ alkyl, $C_2$-$C_{12}$ alkenyl, 0, or —C(O)$R^{17}$;

$R^{17}$ is —OH, $C_1$-$C_{10}$ alkyl, or $C_2$-$C_{12}$ alkenyl; and $R^{18}$ is —OH, $C_1$-$C_6$ alkyl, —NR$^{14}$R$^{15}$, —N$^+$R$^{14}$R$^{15}$R$^{16}$($R^{13}$)$^-$; and

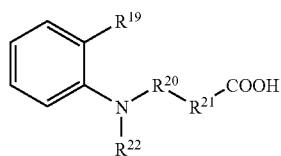

Formula (7)

wherein $R^{19}$ is —NO$_2$ or —C(O)$R^{23}$;

$R^{20}$ is a $C_1$-$C_{12}$ alkylene or $C_1$-$C_{12}$ alkenylene;

$R^{11}$ is a bond or arylene;

$R^{22}$ is H or $C_1$-$C_4$ alkyl; and $R^{13}$ is —OH, $C_1$-$C_6$ alkyl, or —NH$_2$.

Salts of the delivery agent compounds of the present invention may be prepared by methods known in the art. For example, sodium salts may be prepared by dissolving the delivery agent compound in ethanol and adding aqueous sodium hydroxide.

The delivery agent compound may be purified by recrystallization or by fractionation on one or more solid chromatographic supports, alone or linked in tandem. Suitable recrystallization solvent systems include, but are not limited to, acetonitrile, methanol, and tetrahydrofuran. Fractionation may be performed on a suitable chromatographic support such as alumina, using methanol/n-propanol mixtures as the mobile phase; reverse phase chromatography using trifluoroacetic acid/acetonitrile mixtures as the mobile phase; and ion exchange chromatography using water or an appropriate buffer as the mobile phase. When anion exchange chromatography is performed, preferably a 0-500 mM sodium chloride gradient is employed.

Delivery Systems

The composition of the present invention comprises one or more delivery agent compounds of the present invention and a glucagon component. The delivery agent compound and glucagon component are typically mixed prior to administration to form an administration composition.

The administration compositions may be in the form of a liquid. The solution medium may comprise dosing vehicles such as, e.g., water, 25% aqueous propylene glycol, or phosphate buffer. Other dosing vehicles include polyethylene glycol or Klucel. Dosing solutions may be prepared by mixing a solution of the delivery agent compound with a solution of the active agent, just prior to administration. Alternately, a solution of the delivery agent compound (or glucagon) may be mixed with the solid form of glucagon (or delivery agent compound). The delivery agent compound and glucagon may also be mixed as dry powders. The delivery agent compound and glucagon thereof can also be admixed during the manufacturing process.

The dosing solutions may optionally contain additives such as phosphate buffer salts, citric acid, glycols, or other dispersing agents. Stabilizing additives may be incorporated into the solution, preferably at a concentration ranging between about 0.1 and about 20% (w/v).

The administration compositions may alternately be in the form of a solid, such as a tablet, capsule or particle, such as a powder or sachet. Solid dosage forms may be prepared by manually or physically blending the solid form of the delivery agent compound with the solid form of glucagon. Alternately, a solid may be obtained from a solution of the delivery agent compound and glucagon by methods known in the art, such as freeze-drying (lyophilization), precipitation, crystallization, air drying and solid dispersion. Techniques for obtaining active agents (i.e. glucagon) and delivery agents from a solution are disclosed in International Application No. PCT/US03/15629, and U.S. Ser. No. 11/204,756 and 11/204,778 (see, e.g., Example 1). The glucagon and/or delivery agent compound may also be in micronized form, as described in U.S. Ser. No. 11/204,756 and 11/204,778. Each of these applications are hereby incorporated by reference in their entirety.

In one embodiment of the present invention the glucagon/delivery agent composition for tableting is prepared by dissolving a glucagon component and the delivery agent in a solvent (e.g. de-ionized water) and recovering the solid from the solution by lyophilization. In one embodiment of the present invention the a glucagon/delivery agent composition for tableting is prepared by dissolving glucagon and the delivery agent in a solvent (e.g. de-ionized water) and recovering the solid from the solution by air drying.

Alternatively, the administration can be a semi-solid, in the form of a gel, paste, colloid, gelatin, emulsion, suspension and the like.

The administration compositions of the present invention may also include one or more enzyme inhibitors. Such enzyme inhibitors include, but are not limited to, compounds such as actinonin or epiactinonin and derivatives thereof. Other enzyme inhibitors include, but are not limited to, aprotinin (Trasylol) and Bowman-Birk inhibitor.

The amount of glucagon component used in an administration composition of the present invention is an amount effective to treat the target indication. However, the amount can be less than that amount when the composition is used in a dosage unit form because the dosage unit form may contain a plurality of delivery agent compound glucagon agonist compositions or may contain a divided effective amount. The total effective amount can then be administered in cumulative units containing, in total, an effective amount of a glucagon component. Moreover, those skilled in the filed will recognize that an effective amount of glucagon component will vary with many factors including the age and weight of the patient, the patient's physical condition, the blood sugar level, the weight level to be obtained, as well as other factors.

The total amount to be used of glucagon component can be determined by methods known to those skilled in the art. However, because the compositions of the invention may deliver a glucagon component more efficiently than compositions containing glucagon component alone, lower amounts of glucagon component than those used in prior dosage unit forms or delivery systems can be administered to the subject, while still achieving the same blood levels and/or therapeutic effects.

According to one embodiment the amount of glucagon component administered with the delivery agent is an amount sufficient to raise serum glucose to a desired level. In one embodiment, the effective dose of glucagon component (e.g. glucagon) generally ranges from about 1 mg to about 5 mg per dose. Preferably the dosage forms of the present invention contains from about 0.25 mg/kg to about 2 mg/kg/dose of the glucagon component.

The present invention also includes pharmaceutical compositions and dosage forms which include the aforementioned amounts of glucagon component and at least one delivery agent.

Generally an effective amount of delivery agent to facilitate the delivery of a glucagon component is administered with the glucagon component. Generally the amount of delivery agent to glucagon component, on a molar basis, ranges from about 25000:1 to about 50:1 or 1:1 or less, preferably from about 8000:1 to about 100:1 and most preferably from about 4000:1 to about 300:1.

The presently disclosed delivery agent compounds facilitate the delivery of glucagon components (e.g. glucagon) particularly in oral, intranasal, sublingual, intraduodenal, subcutaneous, buccal, intracolonic, rectal, vaginal, mucosal, pulmonary, transdermal, intradermal, parenteral, intraperitoneal, intravenous, intramuscular and ocular systems, as well as traversing the blood-brain barrier. The compositions and dosage unit forms of the present invention may be administered by any of the aforementioned routes.

In one embodiment of the present invention, the compositions and dosage unit forms of the present invention, when administered orally or intraorally to a human, achieve therapeutic levels of glucagon comparable to that obtained via parental, subcutaneous, or intravenous administration of glucagon (when administered without a delivery agent).

Without being bound by any particular theory, applicants believe that when the compositions of the present invention are administered intraorally, there is less dilution and fewer food effects, as compared to oral administration. Intraorally administration can also provide a rapid release of glucagon so as to rapidly reverse depressed serum glucose levels in patients. Alternatively, intraoral administration can also provide a sustained (flat) release profile, which is helpful, for example, to maintain a suitable serum glucose level over a longer time period.

Dosage unit forms can also include any one or combination of excipients, diluents, disintegrants, lubricants, plasticizers, colorants, flavorants, taste-masking agents, sugars, sweeteners, salts, and dosing vehicles, including, but not limited to, water, 1,2-propane diol, ethanol, olive oil, or any combination thereof.

Dosage unit forms for introral administration may contain ingredients known to facilitate introral administration. The intraoral dosage unit form, for example, may be formulated so as to erode gradually over a predetermined time period and release the glucagon and delivery agent at a constant or substantially constant rate. According to one embodiment, the time period ranges from about 0.5 hours to about 24 hours. A bioerodible (hydrolyzable) polymeric carrier that adheres the dosage form to the intraoral mucosa, such as that described in U.S. Published Patent Application No. 2003/0134861 (which is hereby incorporated by reference), can be used, e.g., to provide a sustained release profile. Suitable bioerodible (hydrolyzable) polymeric carriers include, but are not limited to, those which provide a sustained release profile and are compatible with the glucagon and delivery agent. According to one embodiment, the polymeric carrier comprises hydrophilic (water-soluble and water-swellable) polymers that adhere to the wet surface of the buccal mucosa. Non-limiting examples of polymeric carriers useful herein include acrylic acid polymers, e.g., those known as "carbomers" (Carbopol®, which may be obtained from B.F. Goodrich is one such polymer). Other suitable polymers include, but are not limited to: hydrolyzed polyvinylalcohol; polyethylene oxides (e.g., Sentry Polyox® water soluble resins, available from Union Carbide of Midland, Mich.); polyacrylates (e.g., Gantrez®, which may be obtained from GAF of Wayne, N.J.); vinyl polymers and copolymers; polyvinylpyrrolidone; dextran; guar gum; pectins; starches; and cellulosic polymers such as hydroxypropyl methylcellulose (e.g., Methocel®, which may be obtained from the Dow Chemical Company of Midland, Mich.), hydroxypropyl cellulose (e.g., Klucel®, which may also be obtained from Dow), hydroxypropyl cellulose ethers (see, e.g., U.S. Pat. No. 4,704,285 which is incorporated by reference), hydroxyethyl cellulose, carboxymethyl cellulose, sodium carboxymethyl cellulose, methyl cellulose, ethyl cellulose, cellulose acetate phthalate, cellulose acetate butyrate, and the like.

Other components may also be incorporated into the introral dosage forms described herein. The additional components include, but are not limited to, disintegrants, diluents, binders, lubricants, flavoring, colorants, preservatives, and the like. Non-limiting examples of disintegrants are manitol, sodium starch gyycolate, cross-linked polyvinylpyrrolidones, such as crospovidone (e.g., Polyplasdone® XL, which may be obtained from GAF), cross-linked carboxylic methylcelluloses, such as croscarmelose (e.g., Ac-di-sol®, which may be obtained from FMC Corporation of Philadelphia, Pa.), alginic acid, and sodium carboxymethyl starches (e.g., Explotab®, which may be obtained from Edward Medell Co., Inc.), methylcellulose, agar bentonite and alginic acid. Suitable diluents include, but are not limited to, those which are generally useful in pharmaceutical formulations prepared using compression techniques, e.g., dicalcium phosphate dihydrate (e.g., Di-Tab®, which may be obtained from Stauffer), sugars that have been processed by cocrystallization with dextrin (e.g., co-crystallized sucrose and dextrin such as Di-Pakg, which may be obtained from Amstar), lactone, calcium phosphate, cellulose, kaolin, mannitol, sodium chloride, dry starch, powdered sugar and the like. Suitable binders include, but are not limited to, those that enhance adhesion. Non-limiting examples of such binders are starch, gelatin and sugars such as sucrose, dextrose, molasses, and lactose. Non-limiting examples of lubricants include, but are not limited to, stearates (e.g., magnesium stearate) and stearic acid.

In a preferred embodiment, the glucagon and delivery agent are formulated with a starch to form a tablet or film. Amounts of starch to be added to the formulation can be determined by persons of ordinary skill in the art, and include, for example, 1 wt %, 2.5 wt %, 5 wt %, 7.5 wt %, 10 wt %, 20 wt %, 30 wt %, 40 wt %, 50 wt % or 60 wt % of starch, based on the total weight of the formulation.

Preferred intraoral dosage forms include sublingual tablets, creams, ointments and pastes. The tablet, cream, ointment or paste for sublingual delivery comprises a therapeutically effective amount of glucagon and one or more conventional nontoxic carriers suitable for intraoral (e.g., sublingual) drug administration. The intraoral dosage forms of the present invention can be manufactured using conventional processes. The intraoral dosage unit is fabricated to disintegrate rapidly. The time period for complete disintegration of the dosage unit is typically in the range of from about 10 seconds to about 30 minutes, and optimally is less than 5 minutes.

Other components may also be incorporated into the intraoral dosage forms described herein. The additional components include, but are not limited to, binders, disintegrators, wetting agents, lubricants, and the like. Examples of binders that may be used include water, ethanol, polyvinyl pyrrolidone, and starch solution gelatin solution. Suitable disintegrators include, but are not limited to, dry starch, calcium carbonate, polyoxyethylene sorbitan fatty acid esters, sodium lauryl sulfate, stearic monoglyceride, and lactose. Wetting agents, if used, include glycerin, and starches. Suitable lubricants include but are not limited to, stearates and polyethylene glycol. Additional components that may be incorporated into intraoral dosage forms include those known in the art; including those described in *Remington's, The Science and Practice of Pharmacy*, (Gennaro, A. R., ed., 20th edition, 2003, Mack Pub. Co.) which is herein incorporated by reference.

One or more of a solvent, an optional cosolvent, a hydrogel, and an oral mucosal membrane transport enhancing agent, including those described in U.S. Pat. No. 5,284,657 (which is hereby incorporated by reference), may be included in a dosage unit form for, for example, intraoral or oral administration. The solvent may comprise from about 50 percent w/v to about 95 percent w/v or from about 55 percent w/v to about 80 percent w/v of a carrier of a non-toxic alcohol. Suitable non-toxic alcohols include, but are not limited to, ethanol, isopropanol, stearyl alcohol, propylene glycol, and polyethylene glycol (e.g., those having a molecular weight of up to about 650 daltons). Non-toxic alcohols for use in pharmaceutical formulations are well known in the art (cf., for example, Handbook of Pharmaceutical Excipients, published by the American Pharmaceutical Association and The Pharmaceutical Society of Great Britain (1986), which is hereby incorporated by reference in its entirety).

The cosolvent may be selected from water or a pharmaceutically acceptable oil. Suitable oils for use in the unit dosage form of this invention include mineral oil, Neobee™ oil, olive oil, sunflower oil, corn oil, peanut oil and the like. Hydrogels suitable for use in the dosage unit form include hydroxypropyl cellulose, hydroxypropyl methyl cellulose, sodium carboxymethylcellulose (CMC), polyacrylic acid, and poly(methyl methacrylic acid).

Typically, the oral mucosal membrane transport enhancing agent facilitates the absorption of the therapeutic agent (e.g., glucagon) across the mucosal tissues in the oral cavity and directly into the blood stream of the subject. Suitable tissue transport enhancing agents include, but are not limited to, pharmaceutically acceptable and non-toxic essential oils, volatile oils, inorganic acids, and organic acids.

Essential or volatile oils which may be employed in the compositions include, but are not limited to, peppermint oil, spearmint oil, menthol, pepper oil, eucalyptus oil, cinnamon oil, ginger oil, fennel oil, and dill oil. The essential or volatile oil, when employed as the oral mucosal membrane transport enhancing agent in the dosage unit form may be present in a concentration ranging between about 0.5 percent w/v and about 50 percent w/v of the carrier.

Suitable inorganic and organic acids include, but are not limited to, hydrochloric acid, phosphoric acid, aromatic and aliphatic monocarboxylic or dicarboxylic acids of from two to thirty carbon atoms such as acetic acid, citric acid, lactic acid, oleic acid, linoleic acid, lauric acid, plamitic acid, benzoic acid, and salicylic acid. As used in this paragraph, the term "aromatic" carboxylic acid refers to any acid which contains the 6-membered carbocyclic ring system characteristic of benzene, and the term "aliphatic" carboxylic acid refers to any acid which contains a straight-chain or branched chain saturated or unsaturated hydrocarbon backbone.

Liquid compositions for intraoral administration can be formulated into a liquid spray, a liquid drop, a gel or a paste. The desired consistency can be achieved by including in the liquid composition one or more hydrogels, substances that absorb water and produce gels of varying viscosity. Hydrogels suitable for use in pharmaceutical preparations include those known well known in the art, including those described in *Handbook of Pharmaceutical Excipients*, supra, and *Handbook of Water-Soluble Gums and Resins*, ed. by R. L. Davidson, McGraw-Hill Book Co., New York, N.Y. (1980) (both of which are hereby incorporated by reference).

Suitable hydrogels for use in the compositions of this invention include hydroxypropyl cellulose, hydroxypropyl methyl cellulose, sodium carboxymethyl cellulose, polyacrylic acid, poly(methyl methacrylic acid) (PMMA). Preferred hydrogels are cellulose ethers such as hydroxyalkyl-cellulose (e.g., hydroxypropyl cellulose) and hydroxyalkylalkyl-cellulose compounds. Hydroxypropyl cellulose is commercially available in a wide range of viscosity grades sold under the tradename Klucel™ (Hercules, Ltd., London, England). The concentration of the hydroxyalkyl-cellulose is dependent upon the particular viscosity grade used and the desired viscosity of the liquid composition. For example, where the desired viscosity is less than about 1000 centipoise (cps), hydroxypropyl cellulose having an average molecular weight of about 60,000 daltons (i.e., Klucel EF™) can be used. Where the desired viscosity is from about 1000 to about 2500 cps, higher viscosity grades of hydroxypropyl cellulose can be used (e.g., Klucel LF™ and Lucel GF™).

The dosage unit form for intraoral administration may also include collagen, a water soluble additive, and/or other pharmaceutical additives, such as those described in U.S. Pat. No. 5,496,559, which is hereby incorporated by reference. Collagen includes, for example, atelocollagen which is derived from a natural resource, and which is free of a telopeptide which is an antigenic portion of collagen; chemically modified atelocollagen; and naturally-occurring collagen. The collagen which has been chemically derived from the atelocollagen includes, for example, a succinylated collagen and a methylated collagen. The naturally-occurring collagen includes, for example, a collagen from a skin of bovine, a chorda of bovine, a bowel of porcine and sheep, and a human placenta. The collagen can contain a buffer, such as phosphate buffer, citrate buffer, and acetate buffer, and/or a stabilizer. Water soluble additives include for example, proteins, glycoproteins, amino acids, polyamino acids, peptides, saccharides, water-soluble polysaccharides, or a combination thereof. Proteins include, for example, gelatin and albumin. Glycoproteins include, for example, globulin. Amino acids include, for example, aspartic acid, arginine, glycine, and leucine. Polyamino acids and peptides include, for example, polyalanine, polyglycine, sodium polygultamate, sodium polyaspartate, polylysine, and polyleucine. Saccharides, polysaccharides, and water-soluble polysaccharides include, for example, fructose, sucrose, lactose, dextran, cyciodextran, mannitol, and sorbitol. A stabilizer includes one which is used for the proteinaceous physiologically active substances, such as albumin, gelatin, mannitol, and trehalose. Suitable preservatives include, but are not limited to, p-hydroxybenzoates, sorbic acid, and salicylic acid. Suitable buffers include, but are not limited to, citrate buffer, acetate buffer, and phosphate buffer. Suitable sweeteners include, but are not limited to, mannitol, glucose, maltose, starch, and lactose. Suitable flavors include, but are not limited to, aspartic acid, citric acid, and lactic acid. Suitable binder include, but are not limited to, methylcellulose, ethylcellulose, and carboxy methyl cellulose. Suitable suspending agents include, but are not limited to, Tween 20 and Tween 80. Suitable disintegrators include, but are not limited to, glycerol and starch.

Dosage unit forms for intraoral administration may be in the form of a hard candy (e.g. lollipops and mints) or a film, e.g., a slow dissolving film or a fast dissolving film (such as that described in U.S. Pat. No. 6,596,298, which is hereby incorporated by reference). Such films can be prepared by including a film forming agent in the dosage unit form. Suitable film forming agents include, but are not limited to, those described in U.S. Pat. No. 6,596,298 (e.g., pullulan, hydroxypropylmethyl cellulose, hydroxyethyl cellulose, hydroxypropyl cellulose, polyvinyl pyrrolidone, carboxymethyl cellulose, polyvinyl alcohol, sodium alginate, polyethylene glycol, xanthan gum, tragacanth gum, guar gum, acacia gum, arabic gum, polyacrylic acid, methylmethacrylate copolymer, carboxyvinyl polymer, amylose, high amylose starch, hydroxypropylated high amylose starch, dextrin, pectin, chitin, chitosan, levan, elsinan, collagen, gelatin, zein, gluten, soy protein isolate, whey protein isolate, casein and mixtures thereof. According to one embodiment, the concentration of film forming agent in the dosage unit form ranges from about 0.01 to about 99 wt %, from about 30 to about 80 wt %, from about 45 to about 70 wt %, or from about 60 to about 65 wt % (based upon 100% total weight of the film). Administration compositions can also take the form of a pouch that can be placed next to the cheek, or between the lower teeth and lip, similar to smoke-less tobacco products.

The compounds and compositions of the subject invention are useful for administering biologically or chemically active agents to any animals, including but not limited to birds such as chickens; fish, reptiles, insects, mammals, such as rodents, cows, pigs, dogs, cats, primates, and particularly humans.

EXAMPLES

The following examples illustrate the invention without limitation. All parts are given by weight unless otherwise indicated.

Example 1

Aqueous Gel Formulation of a Sublingual Dosage Form 0.5 mL of glucagon powder was dissolved 0.5 mL of deionized water. 50 mg of SNAC powder was added to the glucagon solution until the SNAC was completely dissolved. 10 mg of Klucel powder was slowly added into the above Glucagon/SNAC solution to form a uniform aqueous gel for sublingual dosing.

Example 2

Intraoral Delivery of Glucagon in Beagles

Intraorally Administered Tablet and Aqueous Gel Formulation

An aqueous gel formulation of glucagon, SNAC and Klucel in water was prepared by combining 1 mg glucagon, 100 mg SNAC, 3 mg Klucel BF and 0.5 mL DI water per 10 kg weight of dog by the general procedure described in Example 1.

A sublingual tablet was prepared with 1 mg of glucagon solid powder which was gradually added and blended with about 100 mg Delivery Agent (SNAC) per 10 kg weight of dog model. Upper punch, lower punch and die of Carver 4350 manual pellet press with a Caplet shape model sold by Natoli Engineering Company, Inc. were treated with manitol. About 101 mg of mixed powder was fed into the die and a mini bead shape tablet was made at about 1000 PSI. The resulting solid dosage form was about 5 mm diameter and about 1 mm in height.

The solid dosage form was placed under one dog's tongue and the aqueous gel was used under the other dog's tongue. To facilitate the dissolution of the tablet, about 0.75 ml of saline solution was infused slowly under the tongue on the right side and another 0.75 ml on the left side. One hour post-administration, any remaining formulation was removed by syringe aspiration and the sublingual area was rinsed once with saline solution, removing it afterwards by syringe aspiration.

Two male Beagle dogs weighing between 10.2 and 12.7 kg were fasted overnight before the experiments. The animals were moderately sedated using 0.4-0.8 mg/kg midazolam and 0.03-0.04 mg/kg medetomidine. Once sedated, an intravenous catheter was placed on the cephalic vein for blood sampling.

The aqueous gel dosage form was placed under the dog's tongue and the tablet under the other dog's tongue. One hour post-administration, any remaining formulation was removed by syringe aspiration and the sublingual area was rinsed once with saline solution, removing it afterwards by syringe aspiration.

Blood samples (about 0.5 ml) were collected serially from the cephalic vein, typically at time=0 (predose), 15, 30, 45, 60, 90, 120, 150, and 180 minutes post dose. The samples were placed in serum separating tubes and left at room temperature for 30-45 minutes to allow clotting. The samples were then centrifuged at about 2-8° C. for 10 minutes at 2500 rpm. The resulting serum was transferred into a tube and placed on dry ice and then stored frozen at −70±10° C. until assayed. Results from the animals in each group were averaged for each time point. The results (± standard error) are shown in FIG. 1.

Figure 8:
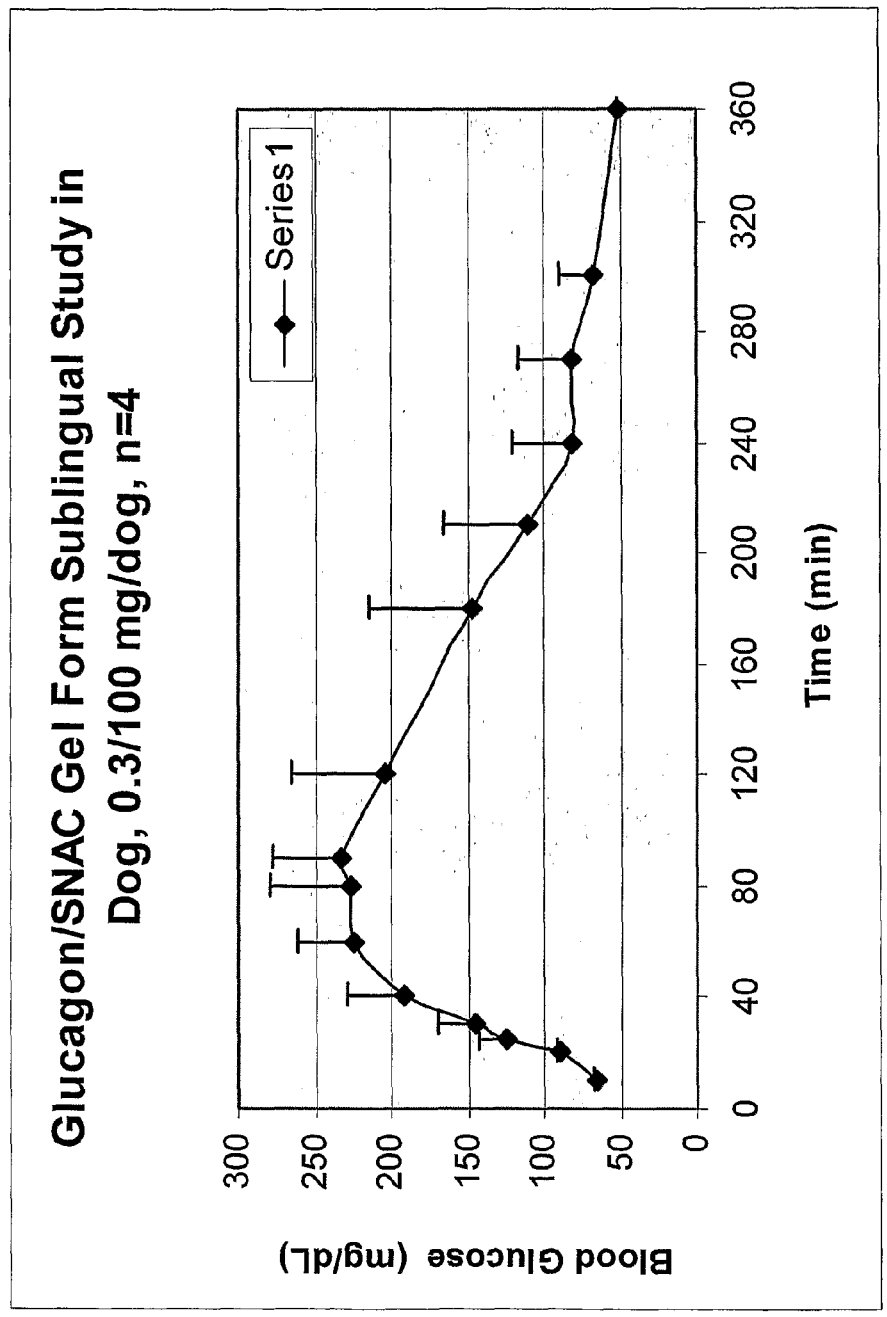
FIG. 8 is a graph of serum glucose concentrations in beagles versus time after intraoral administration of 0.3 mg/kg of glucagon and 100 mg/kg of SNAC.

A separate study was performed based on sublingual administration of an aqueous gel dosage form of 0.3 mg. of glucagon and 100 mg of SNAC, prepared as described in Example 1, to a group of 4 beagles (referred in Table 1 as "0.3/100 gel"). The results are shown in FIG. 8.

Example 3

Intraoral Delivery of Glucagon in Beagle Does

Sublingual Tablet and Intramuscular Glucagon as a Control

A sublingual tablet was prepared with 1 mg of glucagon solid powder which was gradually added and blended with about 20 mg manitol per 10 kg weight of dog model. Upper punch, lower punch and die of Carver 4350 manual pellet press with a Caplet shape model sold by Natoli Engineering Company, Inc. were treated with manitol. About 101 mg of mixed powder was fed into the die and a mini bead shape tablet was made at about 1000 PSI. The resulting solid dosage form was about 5 mm diameter and about 1 mm in height.

Two male Beagle dogs weighing between 10.2 and 12.7 kg were fasted overnight before the experiments. The animals were moderately sedated using 0.4-0.8 mg/kg midazolam and 0.03-0.04 mg/kg medetomidine. Once sedated, an intravenous catheter was placed on the cephalic vein for blood sampling.

The solid dosage form was placed under one dog's tongue. To facilitate the dissolution of the tablet, about 0.75 ml of saline solution was infused slowly under the tongue on the right side and another 0.75 ml on the left side. One hour post-administration, any remaining formulation was removed by syringe aspiration and the sublingual area was rinsed once with saline solution, removing it afterwards by syringe aspiration.

The second dog received an intramuscular injection of glucagon 0.15 mg which was prepared by diluting a 0.1 mg solution of glucagon with DI water (0.1 ml) per 10 kg weight of dog to act as a positive control.

Figure 2:
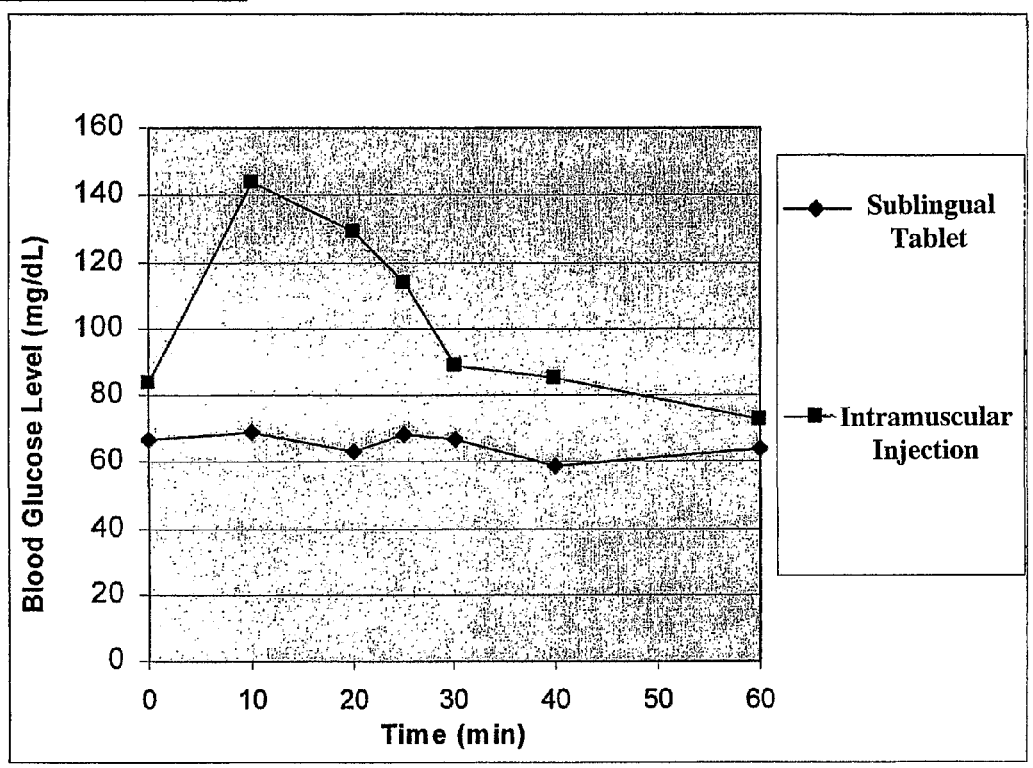
FIG. 2 is a graph of serum glucose concentrations in beagles versus time after sublingual administration of a tablet containing 1 mg of glucagon and 20 mg manitol compared with intramuscular administration of glucagon 0.15 mg.

Blood samples (about 0.5 ml) were collected serially from the cephalic vein, typically at time=0 (predose), 15, 30, 45, 60, 90, 120, 150, and 180 minutes post dose. The samples were placed in serum separating tubes and left at room temperature for 30-45 minutes to allow clotting. The samples were then centrifuged at about 2-8° C. for 10 minutes at 2500 rpm. The resulting serum was transferred into a tube and placed on dry ice and then stored frozen at −70±10° C. until assayed. Results from the animals in each group were averaged for each time point. The results are shown in FIG. 2.

Example 4

Intraoral Delivery of Glucagon in a Beagle Dog

A sublingual tablet was prepared with 0.3 mg of glucagon solid powder which was gradually added and blended with about 30 mg SNAC per 10 kg weight of beagle. Upper punch, lower punch and die of Carver 4350 manual pellet press with a Caplet shape model sold by Natoli Engineering Company, Inc. were treated with mannitol. About 101 mg of mixed powder was fed into the die and a mini bead shape tablet was made at about 1000 PSI. The resulting solid dosage form was about 5 mm diameter and about 1 mm in height.

Two male Beagle dogs weighing between 10.2 and 12.7 kg were fasted overnight before the experiments. The animals were moderately sedated using 0.4-0.8 mg/kg midazolam and 0.03-0.04 mg/kg medetomidine. Once sedated, an intravenous catheter was placed on the cephalic vein for blood sampling.

The solid dosage form was placed under one dog's tongue. To facilitate the dissolution of the tablet, about 0.75 ml of saline solution was infused slowly under the tongue on the right side and another 0.75 ml on the left side. One hour post-administration, any remaining formulation was removed by syringe aspiration and the sublingual area was rinsed once with saline solution, removing it afterwards by syringe aspiration.

The second dog received an intramuscular injection of glucagon 0.15 mg which was prepared by diluting a 0.1 mg solution of glucagon with DI water (0.1 ml) per 10 kg weight of dog to act as a positive control.

Figure 3:
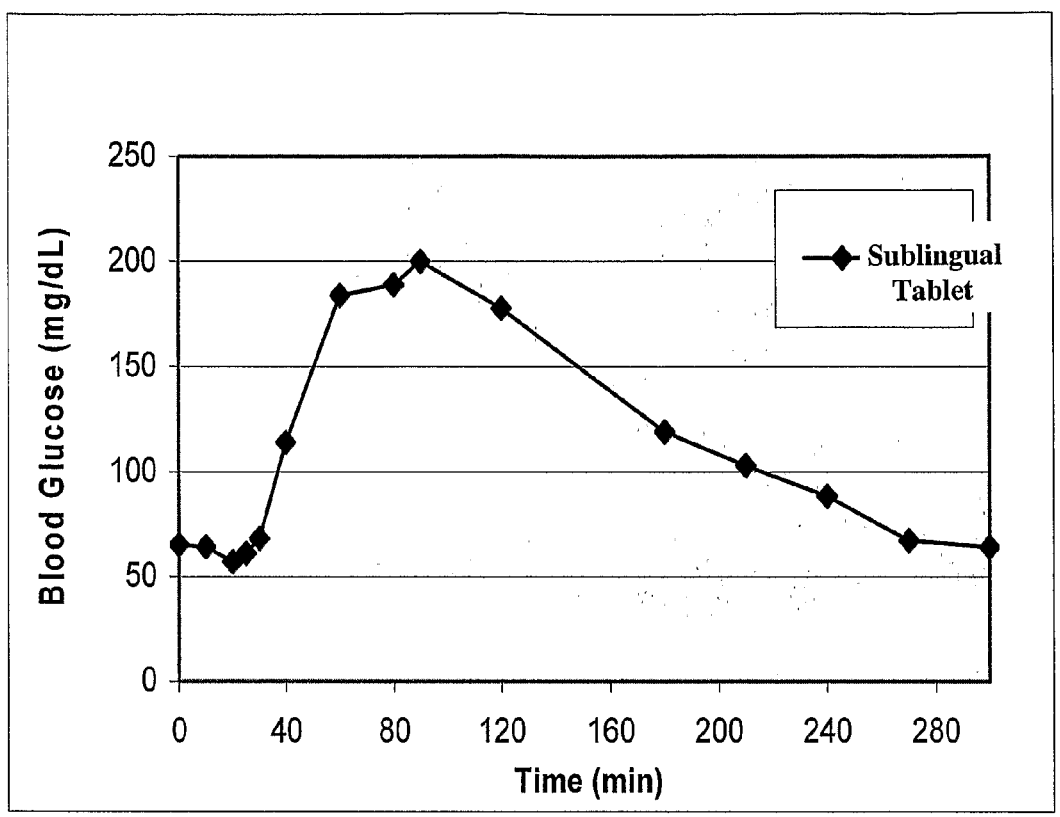
FIG. 3 is a graph of serum glucose concentrations in a beagle versus time after intraoral administration of 0.3 mg/kg of glucagon and 30 mg of SNAC.

Blood samples (about 0.5 ml) were collected serially from the cephalic vein, typically at time=0 (predose), 15, 30, 45, 60, 90, 120, 150, and 180 minutes post dose. The samples were placed in serum separating tubes and left at room temperature for 30-45 minutes to allow clotting. The samples were then centrifuged at about 2-8° C. for 10 minutes at 2500 rpm. The resulting serum was transferred into a tube and placed on dry ice and then stored frozen at −70±10° C. until assayed. Results from the beagle receiving the sublingual tablet are shown in FIG. 3.

Example 5

Dose Optimization Study

Sublingual tablets prepared as in Example 4 were prepared with the following dosage amounts: (a) 0.2 mg glucagon/20 mg of SNAC, (b) 0.3 mg glucagon/30 mg of SNAC, and (c) 1 mg glucagon/100 mg of SNAC. (The first two dosage forms are respectively referred to below in Table 1 as "0.2/20 blend" and "0.3/30 blend".) Each dosage was administered to a group of four beagles (preceded and followed by a washout period).

Figure 4:
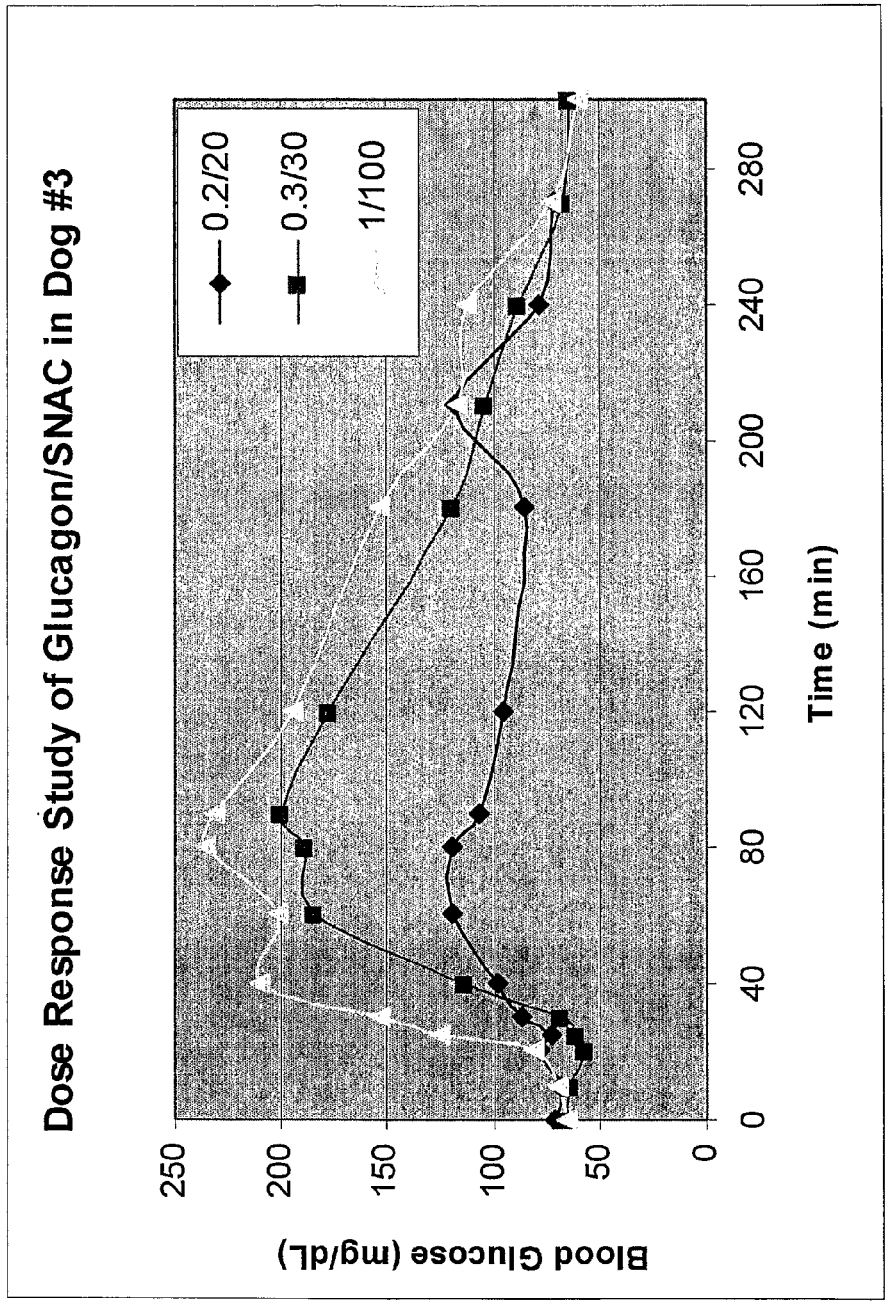
FIGS. 4 and 5 are graphs of serum glucose concentrations in a beagle versus time in a dose response study.
Figure 5:
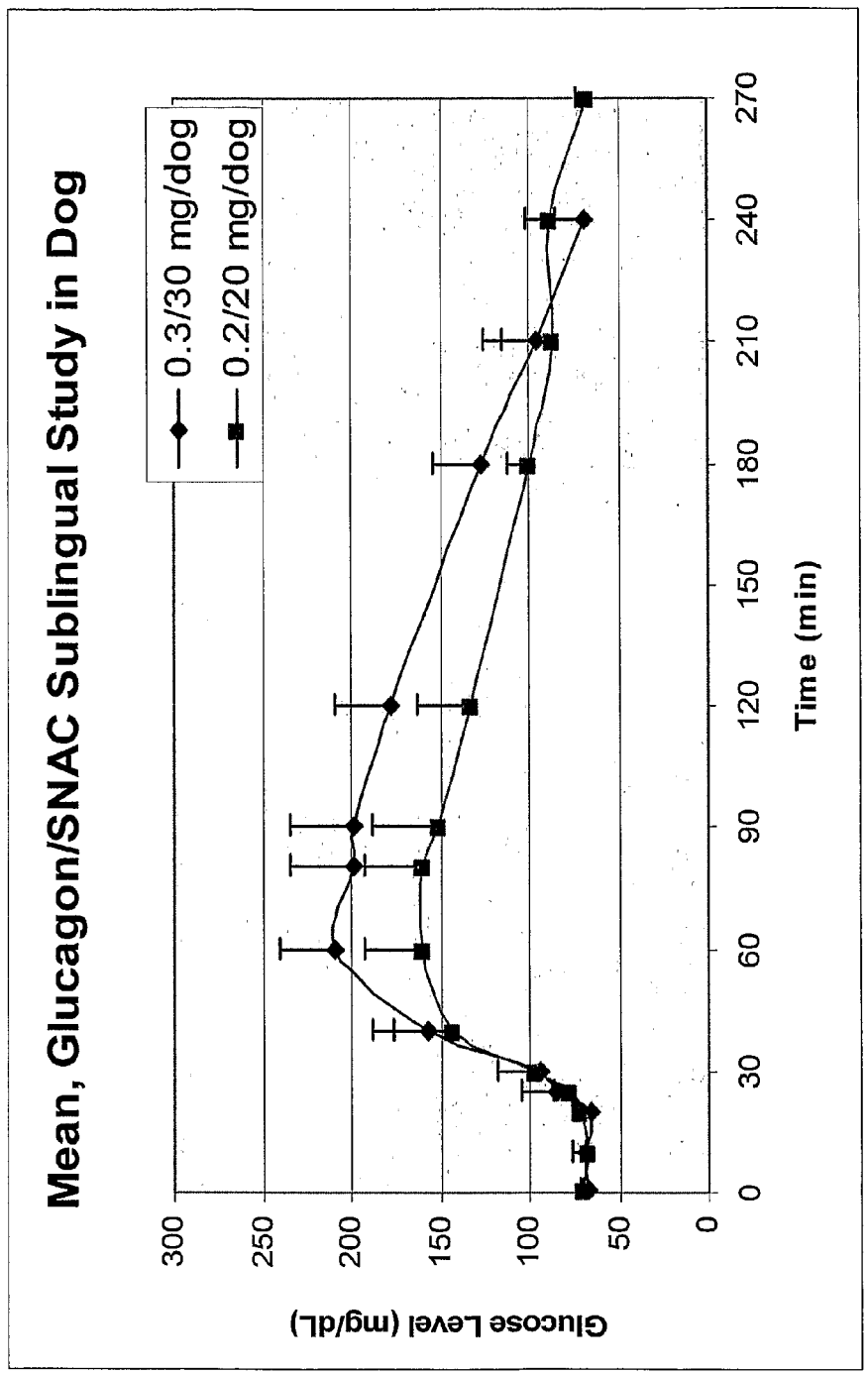

The results of the dose optimization study for one of the beagels (denoted dog #3) are shown in FIG. 4. The results for the 0.2 mg glucagon/20 mg of SNAC, and 0.3 mg glucagon/ 30 mg of SNAC dosages for four beagels (including dog #3) are shown in FIG. 5.

Example 6

Material Preparation Study

Figure 6:
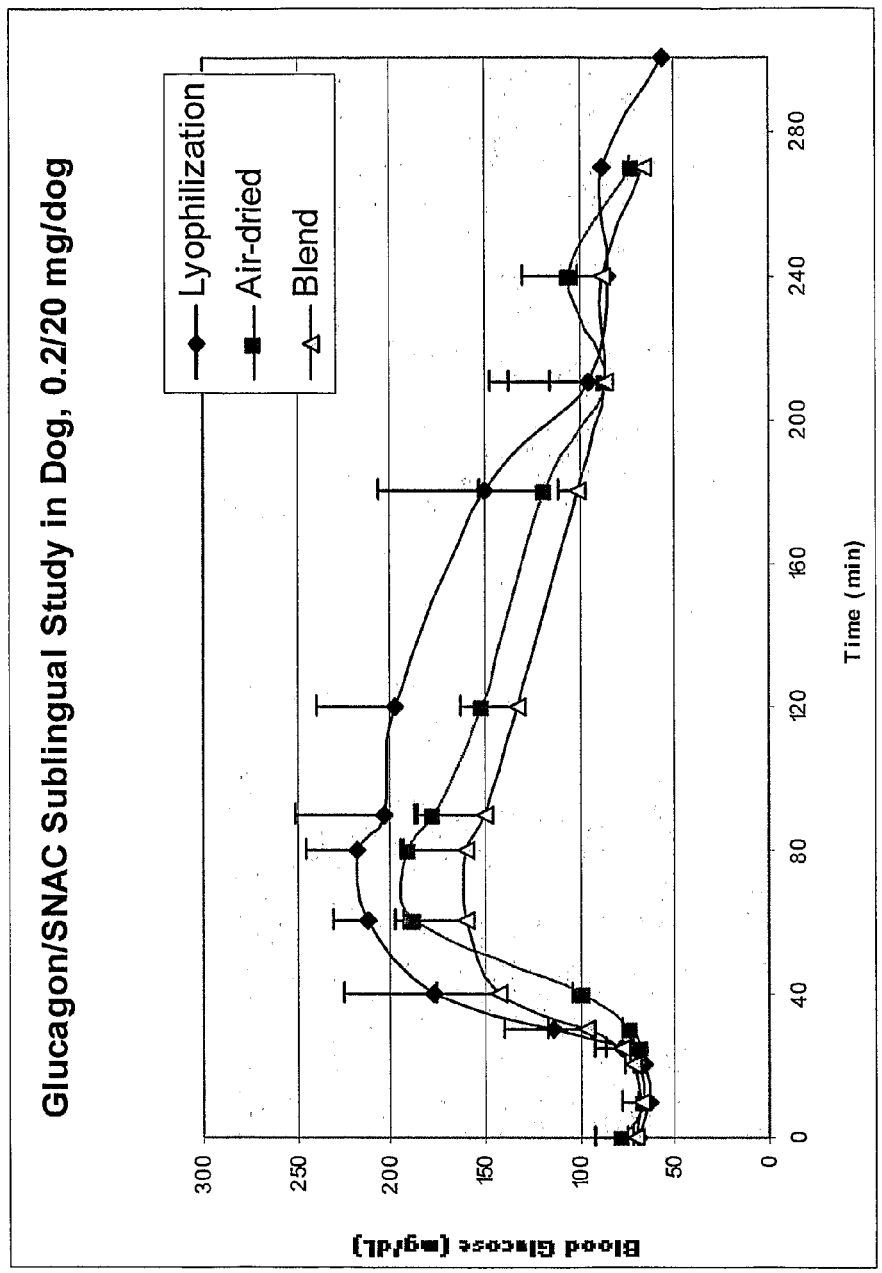
FIGS. 6 and 7 are graphs of serum glucose concentrations in a beagle versus time in a study comparing gel, lyophilization, air-dryed and physical blending formulation techniques.

Three dosage forms of 0.2 mg of glucagon and 20 mg of SNAC were prepared by three different techniques and each was each administered to a group of four beagles preceded and followed by a wash-out period. The first dosage form was prepared by physically blending and tableting the glucagon and SNAC as described in Example 4 (referred in Table 1 below as "0.2/20 blend"). The second dosage form was prepared by dissolving 0.2 mg. of glucagon and 20 mg of SNAC in 0.5 ml of deionized water in small lyophilization bottle and lyophilizing for 48 hours and then tableting the lyophilized powder (referred to in Table 1 below as "0.2/20 lyophilization"). The third dosage form was prepared by dissolving 0.2 mg. of glucagon and 20 mg of SNAC in 0.5 ml of deionized water and air-drying, and tableting the solid obtained from air-drying (referred to in Table 1 below as "0.2/20 air-dried"). The results are shown in FIG. 6.

Figure 7:
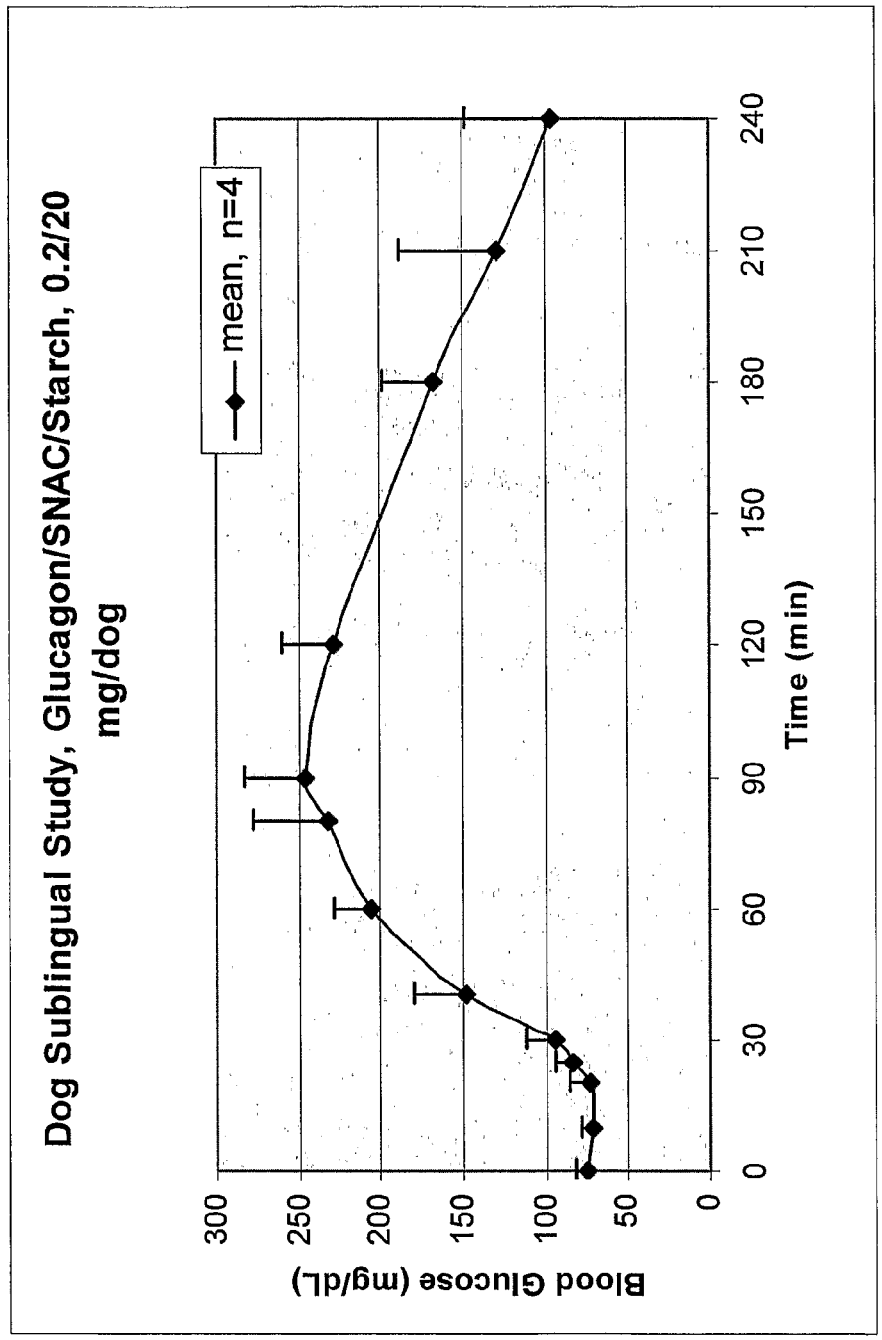

A fourth dosage form was prepared by tableting a blend of 0.2 mg of glucagon, 20 mg of SNAC, with starch as an excipient (referred to in Table 1 below as "0.2/20 starch"). The results when administered to a group of four beagles is shown in FIG. 7.

A brief summary of the results of various formulations described above is shown below in Table 1:

TABLE 1

| Dosage Form | mean ± SD (n = 4) | Tmax (min) | CV |
| --- | --- | --- | --- |
| 0.3/30 blend | 209.25 ± 31 | 60 | 14.81 |
| 0.2/20 blend | 159.75 ± 33.75 | 60 | 20.97 |
| 0.2/20 air-dried | 190.5 ± 3.53 | 80 | 1.86 |
| 0.2/20 lyophilization | 218.25 ± 27.18 | 80 | 12.45 |
| 0.2/20 starch | 245.5 ± 36.83 | 90 | 15 |
| 0.3/100 gel | 232.25 ± 60.62 | 90 | 26.1 |

Any information regarding specific mechanism(s) is provided for only background purposes. The invention should not be construed to be limited, in any way, by any description of the mechanism(s) by which the delivery agents or active agents (e.g., glucagon, glucagon agonists) may function.

The above-mentioned patents, applications, test methods, and publications are hereby incorporated by reference in their entirety.

Many variations of the present invention will suggest themselves to those skilled in the art in light of the above detailed description. All such obvious variations are within the fully intended scope of the appended claims.

We claim:

1. A dosage unit form comprising (a) glucagon, and (b) a delivery agent of the formula

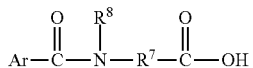

and salts thereof, wherein:
Ar is 2-hydroxyphenyl or 2-hydroxynaphthyl;
Ar is optionally substituted with one or more of —OH, halogen, $C_1$-$C_4$ alkyl, $C_2$-$C_4$ alkenyl, $C_1$-$C_4$ alkoxy or $C_1$-$C_4$ haloalkoxy;
$R^7$ is selected from $C_4$-$C_{20}$ alkyl, $C_4$-$C_{20}$ alkenyl, phenyl, naphthyl, ($C_1$-$C_{10}$ alkyl) phenyl, ($C_2$-$C_{10}$ alkenyl)phenyl, ($C_1$-$C_{10}$ alkyl) naphthyl, ($C_2$-$C_{10}$ alkenyl)naphthyl, phenyl($C_1$-$C_{10}$ alkyl), phenyl($C_2$-$C_{10}$ alkenyl), naphthyl ($C_1$-$C_{10}$ alkyl), or naphthyl($C_2$-$C_{10}$ alkenyl);
$R^8$ is selected from hydrogen, $C_1$-$C_4$ alkyl, $C_2$-$C_4$ alkenyl, $C_1$-$C_4$ alkoxy, and $C_1$-$C_4$ haloalkoxy;
$R^7$ is optionally substituted with $C_1$-$C_4$ alkyl, $C_2$-$C_4$ alkenyl, $C_1$-$C_4$ alkoxy, $C_1$-$C_4$ haloalkoxy, —OH, —SH and —$CO_2R^9$, or any combination thereof;
$R^9$ is hydrogen, $C_1$-$C_4$ alkyl, or $C_2$-$C_4$ alkenyl; and
$R^7$ is optionally interrupted by oxygen, nitrogen, sulfur or any combination thereof,
wherein the dosage unit form is suitable for intraoral administration.

2. The dosage unit form of claim 1, wherein the delivery agent is selected from the group consisting of
the monosodium salt of N-(8-[2-hydroxybenzoyl]-amino) caprylic acid,
the monosodium salt of N-(10-[2-hydroxybenzoyl]-amino)decanoic acid,
the monosodium salt of 8-(2-hydroxy-4-methoxybenzoylamino)octanoic acid,
the monosodium salt of 8-(2,6-dihydroxybenzoylamino) octanoic acid,
the monosodium salt of 8-(2-hydroxy-5-bromobenzoylamino)octanoic acid,
the monosodium salt 8-(2-hydroxy-5-chlorobenzoylamino)octanoic acid,
the monosodium salt of 8-(2-hydroxy-5-iodobenzoylamino)octanoic acid,
the monosodium salt of 8-(2-hydroxy-5-methylbenzoylamino)octanoic acid,
the monosodium salt of 8-(2-hydroxy-5-fluorobenzoylamino)octanoic acid,
the monosodium salt of 8-(2-hydroxy-5-methoxybenzoylamino)octanoic acid,
the disodium salt of N-(10-[2-hydroxybenzoyl]-amino)decanoic acid,
the disodium salt of 8-(2-hydroxy-4-methoxybenzoylamino)octanoic acid, and
the disodium salt of 8-(2-hydroxy-5-methoxybenzoylamino)octanoic acid.

3. The dosage unit form of claim 1 wherein the delivery agent is N-(8-[2-hydroxybenzoyl]-amino)caprylic acid or a pharmaceutically acceptable salt thereof.

4. The dosage unit form of claim 1 wherein the delivery agent is N-(10-[2-hydroxybenzoyl]-amino)decanoic acid or a pharmaceutically acceptable salt thereof.

5. A dosage unit form comprising:
(A) the dosage unit form of claim 1; and
(B) (a) an excipient,
(b) a diluent,
(c) a disintegrant,
(d) a lubricant,
(e) a plasticizer,
(f) a colorant,
(g) a dosing vehicle, or
(h) any combination thereof.

6. The dosage unit form of claim 5, wherein the dosage unit form is in the form of a tablet, a capsule, a particle, a powder, a sachet, or a liquid.

7. The dosage unit form of claim 6, wherein the dosing vehicle is a liquid selected from the group consisting of water, aqueous propylene glycol, phosphate buffer, 1,2-propane diol, ethanol, and any combination thereof.

8. A method for administering an effective amount of glucagon to a patient in need thereof, comprising the step of intraorally administering the dosage unit form according to claim 1.

9. A method of treating hypoglycemia in a patient in need thereof, comprising the step of intraorally administering to the patient an effective amount of the dosage unit form according to claim 1.

10. A method of preparing a dosage unit form comprising the step of mixing (a) glucagon, and (b) a delivery agent of the formula

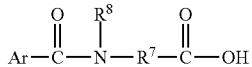

or a salt thereof,
wherein:
Ar is 2-hydroxyphenyl or 2-hydroxynaphthyl;
Ar is optionally substituted with one or more of —OH, halogen, $C_1$-$C_4$ alkyl, $C_2$-$C_4$ alkenyl, $C_1$-$C_4$ alkoxy or $C_1$-$C_4$ haloalkoxy;

R⁷ is selected from C₄-C₂₀ alkyl, C₄-C₂₀ alkenyl, phenyl, naphthyl, (C₁-C₁₀ alkyl) phenyl, (C₂-C₁₀ alkenyl)phenyl, (C₁-C₁₀ alkyl) naphthyl, (C₂-C₁₀ alkenyl)naphthyl, phenyl(C₁-C₁₀ alkyl), phenyl(C₂-C₁₀ alkenyl), naphthyl (C₁-C₁₀ alkyl), or naphthyl(C₂-C₁₀ alkenyl);

R⁸ is selected from hydrogen, C₁-C₄ alkyl, C₂-C₄ alkenyl, C₁-C₄ alkoxy, and C₁-C₄ haloalkoxy;

R⁷ is optionally substituted with C₁-C₄ alkyl, C₂-C₄ alkenyl, C₁-C₄ alkoxy, C₁-C₄ haloalkoxy, —OH, —SH, and —CO₂R⁹, or any combination thereof;

R⁹ is hydrogen, C₁-C₄ alkyl, or C₂-C₄ alkenyl; and

R⁷ is optionally interrupted by oxygen, nitrogen, sulfur or any combination thereof, wherein the dosage unit form is suitable for intraoral administration.

11. The dosage unit form according to claim 1 containing at least about 0.1 mg to about 1 mg of glucagon with at least about 30 mg to about 100 mg of carrier.

12. A dosage unit form comprising (a) glucagon, and (b) a delivery agent of the formula

and salts thereof, wherein:

Ar is 2-hydroxyphenyl or 2-hydroxynaphthyl;

Ar is optionally substituted with one or more of —OH, halogen, C₁-C₄ alkyl, C₂-C₄ alkenyl, C₁-C₄ alkoxy or C₁-C₄ haloalkoxy;

R⁷ is selected from C₄-C₂₀ alkyl, C₄-C₂₀ alkenyl, phenyl, naphthyl, (C₁-C₁₀ alkyl) phenyl, (C₂-C₁₀ alkenyl)phenyl, (C₁-C₁₀ alkyl) naphthyl, (C₂-C₁₀ alkenyl)naphthyl, phenyl(C₁-C₁₀ alkyl), phenyl(C₂-C₁₀ alkenyl), naphthyl (C₁-C₁₀ alkyl), or naphthyl(C₂-C₁₀ alkenyl);

R⁸ is selected from hydrogen, C₁-C₄ alkyl, C₂-C₄ alkenyl, C₁-C₄ alkoxy, and C₁-C₄ haloalkoxy;

R⁷ is optionally substituted with C₁-C₄ alkyl, C₂-C₄ alkenyl, C₁-C₄ alkoxy, C₁-C₄ haloalkoxy, —OH, —SH, and —CO₂R⁹, or any combination thereof;

R⁹ is hydrogen, C₁-C₄ alkyl, or C₂-C₄ alkenyl; and

R⁷ is optionally interrupted by oxygen, nitrogen, sulfur or any combination thereof, wherein the dosage unit form is suitable for sublingual administration.

13. The dosage unit form of claim 12, wherein the delivery agent is selected from the group consisting of the monosodium salt of N-(8-[2-hydroxybenzoyl]-amino)caprylic acid, the monosodium salt of N-(10-[2-hydroxybenzoyl]-amino)decanoic acid, the monosodium salt of 8-(2-hydroxy-4-methoxybenzoylamino)octanoic acid, the monosodium salt of 8-(2,6-dihydroxybenzoylamino)octanoic acid, the monosodium salt of 8-(2-hydroxy-5-bromobenzoylamino)octanoic acid, the monosodium salt 8-(2-hydroxy-5-chlorobenzoylamino)octanoic acid, the monosodium salt of 8-(2-hydroxy-5-iodobenzoylamino)octanoic acid, the monosodium salt of 8-(2-hydroxy-5-methylbenzoylamino)octanoic acid, the monosodium salt of 8-(2-hydroxy-5-fluorobenzoylamino)octanoic acid, the monosodium salt of 8-(2-hydroxy-5-methoxybenzoylamino)octanoic acid, the disodium salt of N-(10-[2-hydroxybenzoyl]-amino)decanoic acid, the disodium salt of 8-(2-hydroxy-4-methoxybenzoylamino)octanoic acid, and the disodium salt of 8-(2-hydroxy-5-methoxybenzoylamino)octanoic acid.

14. The dosage unit form of claim 12, wherein the delivery agent is N-(8-[2-hydroxybenzoyl]-amino)caprylic acid or a pharmaceutically acceptable salt thereof.

15. The dosage unit form of claim 12, wherein the delivery agent is N-(10-[2-hydroxybenzoyl]-amino)decanoic acid or a pharmaceutically acceptable salt thereof.

16. A method of treating hypoglycemia in a patient in need thereof, comprising the step of sublingually administering to the patient an effective amount of the dosage unit form according to claim 12.

17. The dosage unit form of claim 1, wherein the weight ratio of glucagon to delivery agent is about 1:100.

18. The dosage unit form of claim 12, wherein the weight ratio of glucagon to delivery agent is about 1:100.

* * * * *